US009060960B2

(12) United States Patent
Granville et al.

(10) Patent No.: US 9,060,960 B2
(45) Date of Patent: Jun. 23, 2015

(54) TREATMENT OF DISSECTION, ANEURYSM, AND ATHEROSCLEROSIS USING GRANZYME B INHIBITORS

(75) Inventors: David Granville, Port Coquitlam (CA); Rani Cruz, Vancouver (CA); Ciara Chamberlain, Vancouver (CA); Wendy Boivin, Coquitlam (CA); Bruce McManus, Vancouver (CA)

(73) Assignee: The University of British Columbia, Vancouver (CA)

(*) Notice: Subject to any disclaimer, the term of this patent is extended or adjusted under 35 U.S.C. 154(b) by 411 days.

(21) Appl. No.: 12/681,293

(22) PCT Filed: Oct. 1, 2008

(86) PCT No.: PCT/CA2008/001753
§ 371 (c)(1),
(2), (4) Date: Aug. 2, 2010

(87) PCT Pub. No.: WO2009/043170
PCT Pub. Date: Apr. 9, 2009

(65) Prior Publication Data
US 2011/0229546 A1    Sep. 22, 2011

Related U.S. Application Data

(60) Provisional application No. 60/960,480, filed on Oct. 1, 2007, provisional application No. 60/996,138, filed on Nov. 2, 2007.

(51) Int. Cl.
| | | |
|---|---|---|
| A61F 2/00 | (2006.01) | |
| A61K 39/395 | (2006.01) | |
| A61K 9/00 | (2006.01) | |
| A61K 38/00 | (2006.01) | |
| A61P 9/10 | (2006.01) | |
| C07K 14/47 | (2006.01) | |
| C12N 15/11 | (2006.01) | |
| A61K 31/00 | (2006.01) | |
| A61K 31/7088 | (2006.01) | |
| A61L 31/16 | (2006.01) | |

(52) U.S. Cl.
CPC ............. *A61K 31/00* (2013.01); *A61K 31/7088* (2013.01); *A61L 31/16* (2013.01); *A61L 2300/432* (2013.01)

(58) Field of Classification Search
CPC .... A61K 31/00; A61K 31/7088; A61L 31/16; A61L 2300/432
USPC ............. 424/423, 146.1, 158.1, 400; 514/1.1, 514/44 A, 1.9
See application file for complete search history.

(56) References Cited

U.S. PATENT DOCUMENTS

| | | |
|---|---|---|
| 6,699,486 B1 | 3/2004 | Bolla |
| 2003/0148511 A1 | 8/2003 | Ashton-Rickardt et al. |
| 2004/0259172 A1 | 12/2004 | Christgau et al. |
| 2005/0208000 A1 | 9/2005 | Bernstein et al. |
| 2006/0019945 A1 | 1/2006 | Chapman et al. |
| 2007/0104699 A1* | 5/2007 | Rajotte et al. ............... 424/93.21 |
| 2008/0311036 A1* | 12/2008 | Wang et al. .................. 424/1.69 |
| 2010/0317038 A1 | 12/2010 | Granville et al. |

FOREIGN PATENT DOCUMENTS

| | | |
|---|---|---|
| EP | 0580859 A1 | 2/1994 |
| EP | 1163900 A1 | 12/2001 |
| EP | 1281396 A2 | 2/2003 |
| WO | WO-9954737 A1 | 10/1999 |
| WO | 03/065987 | 8/2003 |
| WO | WO-2004067778 A2 | 8/2004 |
| WO | WO-2004100889 A2 | 11/2004 |
| WO | WO-2006093932 A2 | 9/2006 |
| WO | WO-2007036028 A1 | 4/2007 |
| WO | WO-2009055934 A1 | 5/2009 |

OTHER PUBLICATIONS

Choy et al. "Granzyme B Induces Smooth Muscle Cell apoptosis in the Absence of Perforin." Arteriosclerosis, Thrombosis, and Vascular Biology: Journal of the American Heart Association. 2004, 2245-2250.*

Skjelland et al. "Plasma levels of granzyme B are increased in patients with lipid-rich carotid plaques as determined by echogenicity." Atherosclerosis. 2007, 195, e142-e146.*

Upchurch et al. "Abdominal Aortic Aneurysm." American Family Physician. 2006, 73(7), 1198-1204.*

WebMD. "Aortic Aneurysm: Causes, Symptoms, Treatment, and More: Heart Disease and Aortic Aneurysm." http://www.webmd.com/heart-disease/heart-disease-aortic-aneurysm?page=2, accessed on Jun. 11, 2012.*

BusinessHealthGroup. [Retrieved Jan. 16, 2013]. Retrieved from the internet <URL: http://www.businessgrouphealth.org/pub/f31603f5-2354-d714-5126-a6d440aa2f8a>.*

Nataatmadja et al (Sep. 9, 2003). "Abnormal Extracellular Matrix Protein Transport Associated with Increased Apoptosis of Vascular Smooth Muscle Cells in Marfan Syndrome and Bicuspid Aortic Valve Thoracic Aortic Aneurysm". Circulation, 108[suppl II]: II-329-II-334.*

Spaeny-Dekking et al (1998). "Extracellular Granzymes A and B in Humans: Detection of Native Species During CTL Responses In Vitro and In Vivo". The Journal of Immunology, 160: 3610-3616.*

(Continued)

*Primary Examiner* — Anoop Singh
*Assistant Examiner* — Doan Phan
(74) *Attorney, Agent, or Firm* — Christensen O'Connor Johnson PLLC

(57) ABSTRACT

A method of medical treatment or prevention of a vasculopathy, comprising administering a therapeutically effective amount of a granzyme B inhibitor to a subject in need thereof is provided. In other aspects uses of Granzyme B inhibitors for treatment or for preparation of medicaments for treatment of a vasculopathy are provided.

19 Claims, 21 Drawing Sheets

(56) References Cited

OTHER PUBLICATIONS

Chamberlain, Ciara M. (Jun. 2008). Thesis: "Granzyme B in Abdominal Aortic Aneurysm and Aortic Dissection". [Retrieved on Jan. 30, 2013]. Retrieved from the internet <URL: https://circle.ubc.ca/bitstream/handle/2429/5584/ubc_2008_fall_chamberlain_ciara_m.pdf;jsessionid=3DDCEB5E631464CA9626956D62262CB0?sequence=1>.*
The Marfan Foundation (Sep. 16, 2013). "Blood Test on the Horizon to Detect Aortic Aneurysm and Dissection . . ." Retrieved on Mar. 13, 2014. Retrieved from the internet <URL: http://www.marfan.org/about-us/news/2013/09/16/blood-test-horizon-detect-aortic-aneurysm-and-dissection-researchers>.*
Wikipedia. "Fibrillin." Retrieved on Mar. 13, 2013. Retrieved from the internet <URL: http://en.wikipedia.org/wiki/Fibrillin>.*
Wu et al (Jun. 29, 2013) "Molecular mechanisms of thoracic aortic dissection." Journal of Surgical Research, 184: 907-924.*
Marshall et al (Sep. 13, 2013) "Thoracic Aortic Aneurysm Frequency and Dissection are Associated with Fibrillin-1 Fragment Concentration in Circulation." Circulation Research, 113: 1159-1168.*
Sabatier et al (2011). "Fibrillin-3 expression in human development." Matrix Biology, 30: 43-52.*
Singh et al (Nov. 2010). "Fibrillin4 is Required for Plastoglobule Development and Stress Resistance in Apple and Arabidopose." Plant Physiology, 154: 1281-1293.*
World International Property Organization (Canadian Intellectual Property Office as search authority; Karol Gajewski, authorized officer); "International Search Report" for PCT/CA2008/001753; mailing date Nov. 20, 2008; two pages. This U.S. application is a national phase of PCT/CA2008/001753.
Ciara M. Chamberlain et al; "The role of Granzyme B in atheromatous diseases"; Can. J. Physiol. Pharmacol. 2007, 85, pp. 89-95; published online Feb. 9, 2007; 7 pages.
Jonathan C. Choy, et al; "Granzyme B in Atherosclerosis and Transplant Vascular Disease: Association with Cell Death and Atherosclerotic Disease Severity"; Mod. Pathol. 2003, 16(5), pp. 460-470; Copyright United States and Canadian Academy of Pathology; 11 pages.
Ang, et al., "Serpina3n attenuates granzyme B-mediated decorin cleavage and rupture in a murine model of aortic aneurysm," Cell Death Dis. 2011, 2:e209.
Banda, et al., "Mouse macrophage elastase. Purification and characterization as a metalloproteinase," Biochem J. 1981;193(2):589-605.
Buzza, et al., "Extracellular granzymes: current perspectives," Biol Chem. 2006;387(7):827-37.
Choy, et al., "The regulation and consequences of immune-mediated cell death in atheromatous diseases," Cardiovasc Toxicol. 2003;3(3):269-82.
Cruz, et al., "Granzyme B is expressed in macrophage foam cells and plays a key role in atherosclerosis," Vascular Pharmacology, Elsevier, Mmsterdam, NL, 2006, 45(3):191-192.
Cruz, et al., "Granzymes: Major players in vascular remodeling, atherosclerosis and Longevity," Database Biosis; Oct. 16, 2007.
De Boer, et al., "Epstein Barr virus specific T-cells generated from unstable human atherosclerotic lesions: Implications for plaque inflammation," Atherosclerosis. 2006;184(2):322-9.
Hernandez-Pigeon, et al., "UVA induces granzyme B in human keratinocytes through MIF: implication in extracellular matrix remodeling," J Biol Chem. 2007;282(11):8157-64.
Hunger, et al, "Detection of perforin and granzyme B mRNA expressing cells in lichen sclerosus," Exp Dermatol. 2007;16(5):416-20.
Poe, et al., "Human cytotoxic lymphocyte granzyme B. Its purification from granules and the characterization of substrate and inhibitor specificity," J Biol Chem. 1991; 266(1):98-103.
Suidan, et al., Granzyme A released upon stimulation of cytotoxic T lymphocytes activates the thrombin receptor on neuronal cells and astrocytes, Proc Natl Acad Sci U S A. 1994;91(17):8112-6.

Vernooy, et al., "Increased granzyme A expression in type II pneumocytes of patients with severe chronic obstructive pulmonary disease," Am J Respir Crit Care Med. Mar. 1, 2007;175(5):464-72.
Wagsater, et al., "Serine protease inhibitor A3 in atherosclerosis and aneurysm disease," Int J Mol Med. 2012 .994.
Michelle Barry and R. Chris Bleackley, "Cytotoxic T Lymphocytes: All Roads Lead to Death", Nature Reviews / Immunology vol. 2, Jun. 2002, pp. 401-409.
Catherina H. Bird et al., "Selective Regulation of Apoptosis: the Cytotoxic Lymphocyte Serpin Proteinase Inhibitor 9 Protects against Granzyme B-Mediated Apoptosis without Perturbing the Fas Cell Death Pathway", Molecular and Cellular Biology, Nov. 1998, pp. 6387-6398.
Jean-Francois Brunet et al., "The inducible cytotoxic T-lymphocyte-associated gene transcript CTLA-1 sequence and gene localization to mouse chromosome 14", Nature vol. 332, Jul. 17, 1986, pp. 268-271.
Alain Pierre Bruno et al., "Acute myeloblastic leukemic cells acquire cellular cytotoxicity under genotoxic stress: implication of granzyme B and perforin", Blood, vol. 96, No. 5, Sep. 1, 2000, pp. 1914-1920.
Marguerite S. Buzza et al., "Extracellular Matrix Remodeling by Human Granzyme B via Cleavage of Vitronectic, Fibronectin, and Laminin", The Journal of Biological Chemistry, vol. 280, No. 25, Jun. 24, 2005, pp. 23549-23558.
Jonathan C. Choy et al., "Granzyme B Induces Smooth Muscle Cell Apoptosis in the Absence of Perforin: Involvement of Extracellular Matrix Degradation", Arteriosclerosis, Thrombosis, and Vascular Biology, originally published online Oct. 7, 2004, pp. 2245-2250.
Jonathan C. Choy et al., Granzyme B Induces Endothelial Cell Apoptosis and Contributes to the Development of Transplant Vascular Disease, American Journal of Transplantation 2005; 5: pp. 494-499.
Jonathan C. Choy et al., "Granzyme B in Atherosclerosis and Transplant Vascular Disease: Association with Cell Death and Atherosclerotic Disease Severity", The United States and Canadian Academy of Pathology, Inc., vol. 16, No. 5, 2003, pp. 460-470.
Satish Devadas et al., "Granzyme B Is Critical for T Cell Receptor-Induced Cell Death of Type 2 Helper T Cells", Immunity 25, Aug. 2006, pp. 237-247.
R. Goldenbach-Mansky et al., "Raised granzyme B levels are associated with erosions in patients with early rheumatoid factor positive rheumatoid arthritis", Ann Rheum Dis 2005; pp. 715-721.
Ciara M. Chamberlain et al., "the role of Granzyme B in atheromatous diseases", Can. J. Physiol. Pharmacol. 85: 2007, Published online Feb. 9, 2007, pp. 89-95.
Helene Hernandez-Pigeon et al., "Human Keratinocytes Acquire Cellular Cytotoxicity under UV-B Irradiation", Journal of Biological Chemistry, vol. 281, No. 19, May 12, 2006, pp. 13525-13532.
Jonathan W. Heusel et al., "Cytotoxic Lymphocytes Require Granzyme B for the Rapid Induction of DNA Fragmentation and Apoptosis in Allogeneic Target Cells", Cell, vol. 76, Mar. 25, 1994, pp. 977-987.
Gary E. Hill et al., "Aprotinin and Methylprednisolone Equally Blunt Cardiopulmonary Bypass-Induced Inflammation in Humans", Departments of Internal Medicine, Anesthesiology, Surgery, and Perfusion Sciences Education, University of Nebraska Medical Center, Omaha, Neb., 1995, pp. 1658-1662.
Sandra Hodge et al., "Increased Airway Granzyme b and Perforin in Current and Ex-Smoking COPD Subjects", COPD: Journal of Chronic Obstructive Pulmonary Disease, Dec. 2006, pp. 179-187.
M. Huang et al., "Detection of apoptosis-specific autoantibodies directed against granzyme B-induced cleavage fragments of the SS-B (La) autoantigen in sera from patients with primary Sjogren's syndrome", British Society for Immunology, Clinical and Experimental Immunology, 142: (2005), pp. 148-154.
Chih-Min Kam et al., "Granzymes (lymphocyte serine proteases): characterization with natural and synthetic substrates and inhibitors", Biochimica et Biophysica Acta 1477 (2000), pp. 307-323.
Kyoung-Woon Kim et al., "Human rheumatoid synovial fibroblasts promote osteoclastogenic activity by activating RANKL via TLR-2 and TLR-4 activation", ScienceDirect Immunology Letters 110 (2007), pp. 54-64.

(56) References Cited

OTHER PUBLICATIONS

M C Kraan et al., "T cells, fibroblast-like synoviocytes, and granzyme B+ cytotoxic cells are associated with joint damage in patients with recent onset rheumatoid arthritis", Ann Rheum Dis. 2004; 63, pp. 483-488.

Sami Mahrus and Charles S. Craik, "Selective Chemical Functional Probes of Granzymes A and B Reveal Granzyme B Is a Major Effector of Natural Killer Cell-Mediated Lysis of Target Cells", Chemistry & Biology, vol. 12, May 2005, pp. 567-577.

Paula A. Revell et al., "Granzyme B and the Downstream Granzymes C and/or F Are Important for Cytotoxic Lymphocyte Functions", Journal of Immunology; 174 (2005), pp. 2124-2131.

A. Rosen and L. Casciola-Rosen, "Altered Autoantigen Structure in Sjogren's Syndrome: Implications for the Pathogenesis of Autoimmune Tissue Damage", Critical Reviews in Oral Biology & Medicine 15: (2004), pp. 156-164.

Rabia Sattar et al., "Bioinformatics of granzymes: sequence comparison and structural studies on granzyme family by homology modeling", Biochemical and Biophysical Research Communications 308 (2003), pp. 726-735.

Mona Skjelland et al., "Plasma levels of granzyme B are increased in patients with lipid-rich carotid plaques s determined by echogenicity", Atherosclerosis 195 (2007), pp. e142-e146.

Jiuru Sun et al., "A Cytosolic Granzyme B Inhibitor Related to the Viral Apoptotic Regulator Cytokine Response Modifier A Is Present in Cytotoxic Lymphocytes", The Journal of Biological Chemistry, vol. 271, No. 44, Nov. 1, 1996, pp. 27802-27809.

Jiuru Sun et al., A New Family of 10 Murine Ovalbumin Serpins Includes Two Homologs of Proteinase Inhibitor 8 and Two Homologs of the Granzyme B Inhibitor (Proteinase Inhibitor 9), The Journal of Biological Chemistry, vol. 272, No. 24, Jun. 13, 1997, pp. 15434-15441.

Marielle Thewissen et al., "Analyses of Immunosenescent markers in patients with autoimmune disease", Clinical Immunology (2007) 123, pp. 209-218.

Guy M. Tremblay et al., "Granzyme Activity in the Inflamed Lung Is Not Controlled by Endogenous Serine Proteinase Inhibitors", The Journal of Immunology (2000); 165, pp. 3966-3969.

R. Tsuru et al., "Increased granzyme B production from peripheral blood mononuclear cells in patients with acute coronary syndrome", Heart 2008 94: originally published online Jun. 25, 2007, pp. 305-310.

Joyce Villanueva et al., "Natural killer cell dysfunction is a distinguishing feature of systemic onset juvenile rheumatoid arthritis and macrophage activation syndrome", Arthritis Res. Ther. 2005, 7, pp. R30-R37.

Christopher A. Willoughby et al., "Discovery of Potent, Selective Human Granzyme B Inhibitors that Inhibit CTL Mediated Apoptosis", Bioorganic & Medicinal Chemistry Letters 12 (2002), pp. 2197-2200.

Dai, E., et al., "Reduced Plaque Growth After Infusion of Unique Poxviral Serpins in Rat Models of Angioplasty Injury and Aortic Allograft Transplant," Canadian Journal of Cardiology 16(Supplement F):150F-151F, Sep. 2000.

Office Action mailed Mar. 26, 2013, issued in corresponding Japanese Application No. 2010-527305, filed Oct. 1, 2008, 7 pages.

\* cited by examiner

A.

Negative Control (20X)

B.

Aneurysm Tissue Stained with GrB (20X)

TREATMENT OF DISSECTION, ANEURYSM, AND ATHEROSCLEROSIS USING GRANZYME B INHIBITORS

TECHNICAL FIELD

This invention relates to the field of blood vessel pathology. More particularly to the treatment of blood vessel pathology by inhibiting granzyme B.

BACKGROUND

Granzymes are a highly conserved group of serine proteases, with five members (A, B, H, K and M) in humans and ten members (A-G, K, M-N) in mice (Sattar R. et al. Biochem Biophys Res Commun 308, 726-35 (2003). Granzyme B (GrB) or cytotoxic T-lymphocyte (CTL)-associated gene transcript-1—Brunet J F. et al. Nature 322, 268-71 (1986)), has been reported as being involved in anti-viral and anti-tumour functions, and is associated with autoimmunity, transplant rejection, graft-versus-host disease, and thymocyte development (Barry M. & Bleackley R C. Nat Rev Immunol 2, 401-9 (2002)).

GrB is reported to have a contribution to CTL-mediated target cell apoptosis. GrB-deficient mice possess a normal phenotype, with the exception of a slightly reduced CTL-mediated target cell apoptosis, anti-viral responses and tumour cell clearance (Revell P A. et al. J Immunol 174, 2124-31 (2005); and Heusel J W. et al. Cell 76, 977-87 (1994)), suggesting a redundancy in immune mediated cell removal. GrB-deficient recipient mice exhibit reduced allograft vasculopathy (Choy J C. et al. Am J Transplant 5, 494-9 (2005)), and its deficiency in mice leads to increased susceptibility to allergen-induced asthma (Devadas, S. et al. Immunity 25, 237-47 (2006)). Choy J C. et al. reported patients with advanced atherosclerosis and transplant vascular disease showed GrB increases with disease severity, and the occasional SMC in advanced plaques, but extracellular GrB staining was absent in advanced disease, while no GrB was observed in healthy arteries (Mod Pathol 16, 460-70 (2003)). In a later publication Choy et al. associate GrB with apoptosis by mediating proteolysis of extracellular proteins through activated T cells and report that cytotoxic T cells localize to medial SMCs in aortic aneurysms (Arterioscler. Thromb. Vasc. Biol.; 24; 2245-2250, (2004)). Skjelland, et al. teach that plasma levels of GrB are increased in patients with lipid rich carotid plaques (Atherosclerosis, 195:e142-e146 (2007)) Kim et al. show that macrophages express granzyme B in the lesion areas of atherosclerosis and rheumatoid arthritis (Immunology Letters, 111, 57-65, (2007)). GrB has also been reported to be associated to cleave vitronectin, fibronectin, and laminin (Buzza M S. et al. JBC vol. 280(25):23549-23558 (2005)). Furthermore, GrB has been associated with acute coronary syndrome (Tsuru R. et al. Heart 94:305-310 (2008) e-published Jun. 25, 2007). GrB has also been reported on in association with rheumatoid arthritis (Goldbach-Mansky et al. Ann Rheum Dis. 64:715-721 (2005); Kraan et al. Ann Rheum Dis 63:483-488 (2004); Villanueva et al. Arthritis Res Ther 7:R30-R37 (2005); and Thewissen et al. Clinical Immunology 123:209-218 (2007)) in inflammatory lung disease (Tremblay et al. J Immunology 165:3966-3969 (2000)), in Chronic Obstructive Pulmonary Disease (Hodge et al. J. of COPD 3:179-187 (2006), and Sjögren's Syndrome (Rosen et al. Crit Rev Oral Biol Med 15(3):156-164 (2004); and Huang et al. Clin Exp Immun 142:148-154 (2005)). GrB inhibitors are also known (for example WO 03/065987).

SUMMARY

In one aspect of the present invention, there is provided a method of preventing or treating a vasculopathy in a subject in need thereof, the method including administering to the subject a Granzyme B (GrB) inhibitor. The method may further comprise selecting a subject having a GrB plasma level of >40 pg/ml. A subject may also be selected on the basis of a GrB plasma level of >41 pg/ml. A subject may also be selected on the basis of a GrB plasma level of >42 pg/ml. A subject may also be selected on the basis of a GrB plasma level of >43 pg/ml. A subject may also be selected on the basis of a GrB plasma level of >44 pg/ml. A subject may also be selected on the basis of a GrB plasma level of >45 pg/ml. A subject may also be selected on the basis of a GrB plasma level of >46 pg/ml. A subject may also be selected on the basis of a GrB plasma level of >47 pg/ml. A subject may also be selected on the basis of a GrB plasma level of >48 pg/ml. A subject may also be selected on the basis of a GrB plasma level of >49 pg/ml. A subject may also be selected on the basis of a GrB plasma level of >50 pg/ml. A subject may also be selected on the basis of a GrB plasma level of >55 pg/ml. A subject may also be selected on the basis of a GrB plasma level of >60 pg/ml. A subject may also be selected on the basis of a GrB plasma level of >65 pg/ml. A subject may also be selected on the basis of a GrB plasma level of >70 pg/ml.

The method may further comprise selecting a subject having an aortic aneurysm with a diameter of at least 3 cm. A subject may also be selected on the basis of an aortic aneurysm with a diameter of at least 3.1 cm. A subject may also be selected on the basis of an aortic aneurysm with a diameter of at least 3.2 cm. A subject may also be selected on the basis of an aortic aneurysm with a diameter of at least 3.3 cm. A subject may also be selected on the basis of an aortic aneurysm with a diameter of at least 3.4 cm. A subject may also be selected on the basis of an aortic aneurysm with a diameter of at least 3.5 cm. A subject may also be selected on the basis of an aortic aneurysm with a diameter of at least 3.6 cm. A subject may also be selected on the basis of an aortic aneurysm with a diameter of at least 3.7 cm. A subject may also be selected on the basis of an aortic aneurysm with a diameter of at least 3.8 cm. A subject may also be selected on the basis of an aortic aneurysm with a diameter of at least 3.9 cm. A subject may also be selected on the basis of an aortic aneurysm with a diameter of at least 4.0 cm.

The method may further comprise selecting a subject having a cerebral aneurysm with a diameter of at least 0.5 cm. A subject may also be selected on the basis of a cerebral aneurysm with a diameter of at least 0.6 cm. A subject may also be selected on the basis of a cerebral aneurysm with a diameter of at least 0.7 cm. A subject may also be selected on the basis of a cerebral aneurysm with a diameter of at least 0.8 cm. A subject may also be selected on the basis of a cerebral aneurysm with a diameter of at least 0.9 cm.

The method may further comprise selecting a subject having an atherosclerotic plaque with a diameter of at least 4 cm. A subject may also be selected on the basis of an atherosclerotic plaque with a diameter of at least 4.5 cm. A subject may also be selected on the basis of an atherosclerotic plaque with a diameter of at least 5.0 cm. A subject may also be selected on the basis of an atherosclerotic plaque with a diameter of at least 5.5 cm.

The method may further comprise selecting a subject having an aortic dissection with a diameter of at least 3 cm. A subject may also be selected on the basis of an aortic dissection with a diameter of at least 3.5 cm. A subject may also be selected on the basis of an aortic dissection with a diameter of at least 4.0 cm. A subject may also be selected on the basis of an aortic dissection with a diameter of at least 4.5 cm. A subject may also be selected on the basis of an aortic dissection with a diameter of at least 5.0 cm. A subject may also be selected on the basis of an aortic dissection with a diameter of at least 5.5 cm.

In further aspect of the present invention, there is provided a use of a GrB inhibitor in the manufacture of a medicament for the prevention or treatment of a vasculopathy in a subject in need thereof.

In further aspect of the present invention, there is provided a use of a GrB inhibitor for the prevention or treatment of a vasculopathy in a subject in need thereof.

In further aspect of the present invention, there is provided a use of a pharmaceutical composition including a GrB inhibitor for the prevention or treatment of a vasculopathy in a subject in need thereof.

The use may further comprise selecting a subject having an aortic aneurysm with a diameter of at least 3 cm. A subject may also be selected on the basis of an aortic aneurysm with a diameter of at least 3.1 cm. A subject may also be selected on the basis of an aortic aneurysm with a diameter of at least 3.2 cm. A subject may also be selected on the basis of an aortic aneurysm with a diameter of at least 3.3 cm. A subject may also be selected on the basis of an aortic aneurysm with a diameter of at least 3.4 cm. A subject may also be selected on the basis of an aortic aneurysm with a diameter of at least 3.5 cm. A subject may also be selected on the basis of an aortic aneurysm with a diameter of at least 3.6 cm. A subject may also be selected on the basis of an aortic aneurysm with a diameter of at least 3.7 cm. A subject may also be selected on the basis of an aortic aneurysm with a diameter of at least 3.8 cm. A subject may also be selected on the basis of an aortic aneurysm with a diameter of at least 3.9 cm. A subject may also be selected on the basis of an aortic aneurysm with a diameter of at least 4.0 cm.

The use may further comprise selecting a subject having a cerebral aneurysm with a diameter of at least 0.5 cm. A subject may also be selected on the basis of a cerebral aneurysm with a diameter of at least 0.6 cm. A subject may also be selected on the basis of a cerebral aneurysm with a diameter of at least 0.7 cm. A subject may also be selected on the basis of a cerebral aneurysm with a diameter of at least 0.8 cm. A subject may also be selected on the basis of a cerebral aneurysm with a diameter of at least 0.9 cm.

The use may further comprise selecting a subject having an atherosclerotic plaque with a diameter of at least 4 cm. A subject may also be selected on the basis of an atherosclerotic plaque with a diameter of at least 4.5 cm. A subject may also be selected on the basis of an atherosclerotic plaque with a diameter of at least 5.0 cm. A subject may also be selected on the basis of an atherosclerotic plaque with a diameter of at least 5.5 cm.

The use may further comprise selecting a subject having an aortic dissection with a diameter of at least 3 cm. A subject may also be selected on the basis of an aortic dissection with a diameter of at least 3.5 cm. A subject may also be selected on the basis of an aortic dissection with a diameter of at least 4.0 cm. A subject may also be selected on the basis of an aortic dissection with a diameter of at least 4.5 cm. A subject may also be selected on the basis of an aortic dissection with a diameter of at least 5.0 cm. A subject may also be selected on the basis of an aortic dissection with a diameter of at least 5.5 cm.

The vasculopathy may be selected from one or more of: atherosclerosis; aneurysm; and dissection. The vasculopathy may be an aortic aneurysm. The vasculopathy may be a cerebral aneurysm. The vasculopathy may be an aortic dissection. The vasculopathy may be a cerebral dissection. The vasculopathy may be atherosclerosis.

The GrB inhibitor may be formulated for oral administration. The GrB inhibitor may be formulated for administration by injection. The GrB inhibitor may be formulated for topical administration. The GrB inhibitor may be formulated for topical application to a device. The topical application to a device may be a coating. The device may be selected from: a stent; a clip; a catheter; and a coil. The subject may be a human. The administering may be to the tissue of the blood vessel or intima of a subject.

In further aspect of the present invention, there is provided a method for diagnosis of a vasculopathy in a subject suspected of having a vasculopathy or having a vasculopathy, the method including: determining the concentration of GrB in a blood plasma or serum sample from the subject; and comparing the concentrations to the corresponding concentration in a control sample, wherein an elevated concentration of GrB is indicative of chronic inflammatory disease.

The method may further include determining the concentration of one or more of: fibronectin; and fibrillin; with reference to the control sample as indicative of chronic inflammatory disease. The concentration of GrB, fibronectin and/or fibrillin may be determined by an immunodiagnostic assay. The immunodiagnostic assay may be an enzyme-linked immunosorbent assay (ELISA), enzyme-linked immunosorbent spot (ELISPOT), dot blot, Western blot, or other proteomics assay etc. The subject may have a GrB blood plasma concentration >40 pg/ml and/or a fibronectin blood plasma concentration >400 µg/ml as an indication of a vasculopathy. The fibronectin or fibrillin, may be a fibronectin degradation product or a fibrillin degradation product. The method may further include one or more of: diagnostic imaging; clinical diagnosis and alternative laboratory diagnostics.

A GrB concentration greater than about 40 pg/ml may be considered indicative of vasculopathy. A GrB concentration greater than about 41 pg/ml may be considered indicative of vasculopathy. A GrB concentration greater than about 42 pg/ml may be considered indicative of vasculopathy. A GrB concentration greater than about 43 pg/ml may be considered indicative of vasculopathy. A GrB concentration greater than about 44 pg/ml may be considered indicative of vasculopathy. A GrB concentration greater than about 45 pg/ml may be considered indicative of vasculopathy. A GrB concentration greater than about 50 pg/ml may be considered indicative of vasculopathy. A GrB concentration greater than about 55 pg/ml may be considered indicative of vasculopathy. A GrB concentration greater than about 60 pg/ml may be considered indicative of vasculopathy. A GrB concentration greater than about 65 pg/ml may be considered indicative of vasculopathy. A GrB concentration greater than about 70 pg/ml may be considered indicative of vasculopathy. A GrB concentration greater than about 75 pg/ml may be considered indicative of vasculopathy. A GrB concentration greater than about 80 pg/ml may be considered indicative of vasculopathy. A GrB concentration greater than about 90 pg/ml may be considered indicative of vasculopathy. A GrB concentration greater than about 100 pg/ml may be considered indicative of vasculopathy.

In a further aspect of the present invention, there are provided kits, commercial packages and uses for the diagnosis of a vasculopathy. The kits and commercial packages may also include one or more of: reagents, antibodies, normal controls, a listing of normal levels and those associated with a diagnosis of one or more of a vasculopathy, and/or instructions for their use. The methods may also be used in conjunction with known diagnostic methods.

DETAILED DESCRIPTION

Figure 1:
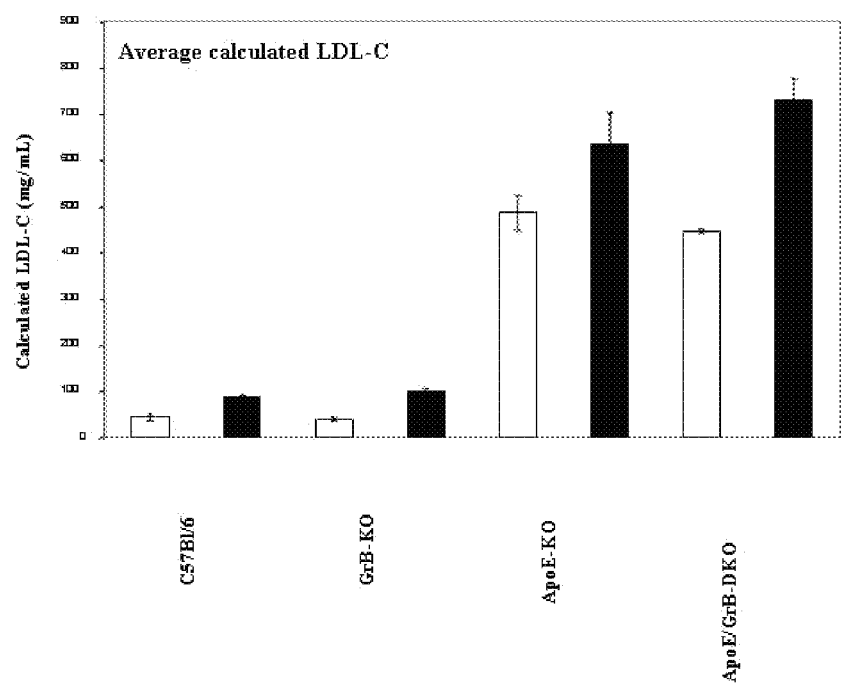
FIG. 1 is a bar graph showing the average calculated LDL-C in the plasma of C57/B1/6, GrB KO, ApoE KO or ApoE/GrB DKO mice. White bars represent mice fed a normal chow diet; black bars represent mice fed a Western diet. N=3 for each group. Calculated LDL-C (mg/ml) is the Y-axis.

The samples from the subject and the normal samples from the normal subject may be blood plasma samples, bronchiole lavages or other bodily fluids. A "subject" and a "normal subject" differ, at least in part, in that the normal subject is known to not have, or at least suspected of not having, a vasculopathy, and is not at risk for having or developing a vasculopathy as described herein. Provided that the sample from the subject and the normal sample from the normal subject are taken from the same tissue type or bodily fluid type, then the sample from the subject may be compared to the normal sample from the normal subject for the purpose of identifying a subject for treatment or prevention of a vasculopathy as described herein.

In general, the higher the level of granzyme B a subject has, the more likely it is that the subject is likely to suffer ill effects from the vasculopathy. Also, in general, the higher the level of granzyme B subject has the more likely it is that the subject is at risk for or has a vasculopathy as described herein. The higher the level of granzyme B in a subject, the more likely it is that the subject is at risk for developing the vasculopathy as described herein if the subject does not already have the vasculopathy as described herein. The higher the level of granzyme B in a subject, the more likely it is that the vasculopathy and/or vasculopathy symptoms will manifest themselves more quickly and severely.

Alternative methods for identifying a subject that is at risk for developing a vasculopathy as described herein may comprise: identifying a level of granzyme B in a sample from the subject; wherein the subject is at risk for developing a vasculopathy as described herein when the level of granzyme B in the sample from the subject is higher than about 40 pg/ml. If a subject has a granzyme B level of about 40 pg/ml or more then this may be indicative of the subject having a vasculopathy as described herein or the subject being at risk for developing or increasing the rate of onset of the vasculopathy as described herein. A level of about 60 pg/ml or more may be indicative of the subject having a vasculopathy as described herein or the subject being at risk for developing or increasing the rate of onset of a vasculopathy as described herein. A level of about 80 pg/ml or more may be indicative of the subject having a vasculopathy as described herein or the subject being at risk for developing or increasing the rate of onset of a vasculopathy as described herein. A level of about 100 pg/ml or more may be indicative of the subject having a vasculopathy as described herein or the subject being at risk for developing or increasing the rate of onset of a vasculopathy as described herein. A level of about 120 pg/ml or more may be indicative of the subject having a vasculopathy as described herein or the subject being at risk for developing or increasing the rate of onset of a vasculopathy as described herein. A level of about 140 pg/ml or more may be indicative of the subject having a vasculopathy as described herein or the subject being at risk for developing or increasing the rate of onset of a vasculopathy as described herein. A subject having a granzyme B level of between about 40 pg/ml to 140 pg/ml (and all individual values in between are specifically disclosed by this range (for example: 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, and 140) may be indicative of the subject having a vasculopathy as described herein or the subject being at risk for developing or increasing the rate of onset of a vasculopathy as described herein. A subject having a granzyme B level of between about 50 pg/ml to 140 pg/ml may be indicative of the subject having a vasculopathy as described herein or the subject being at risk for developing or increasing the rate of onset of a vasculopathy as described herein. A subject having a granzyme B level of between about 70 pg/ml to 140 pg/ml may be indicative of the subject having a vasculopathy as described herein or the subject being at risk for developing or increasing the rate of onset of a vasculopathy as described herein. A subject having a granzyme B level of between about 90 pg/ml to 140 pg/ml may be indicative of the subject having a vasculopathy as described herein or the subject being at risk for developing or increasing the rate of onset of a vasculopathy as described herein. A subject having a granzyme B level of between about 110 pg/ml to 140 pg/ml may be indicative of the subject having a vasculopathy as described herein or the subject being at risk for developing or increasing the rate of onset of a vasculopathy as described herein.

Methods for identifying a subject being at risk for or having a vasculopathy as described herein, may be supplemented by, in addition to comparing a level of granzyme B in a first sample from the subject as described herein, identifying a level of fibronectin, elastin and/or fibrillin in a second sample from the subject, identifying a level fibronectin, elastin and/or fibrillin in a second normal sample from the normal subject not at risk for or having a vasculopathy as described herein and comparing the level of fibronectin, elastin and/or fibrillin in the second sample from the subject to the level of fibronectin, elastin and/or fibrillin in the second normal sample from the normal subject. The subject is more likely to be at risk for or having a vasculopathy as described herein when the level of fibronectin, elastin and/or fibrillin in the second sample from the subject is lower than the level of fibronectin, elastin and/or fibrillin in the second normal sample from the normal subject. Granzyme B cleaves extracellular matrix proteins and when a subject has an elevated or high level of granzyme B as described above, the level of extracellular matrix proteins in the subject will be reduced by the action of granzyme B. The longer that high levels of granzyme B have been active, the lower the tissue levels of extracellular matrix proteins will be.

An alternative method for identifying a subject being at risk or having a vasculopathy as described herein comprises: identifying a level of granzyme B in a first sample from the subject; and identifying a level of fibronectin in a second sample from the subject, wherein the subject is at risk for developing or has a vasculopathy as described herein when a) the level of granzyme B in the first sample from the subject is higher than about 40 pg/ml, is higher than about 60 pg/ml, is higher than about 80 pg/ml, is higher than about 100 pg/ml, is higher than about 120 pg/ml, is higher than about 140 pg/ml, is higher than about 160 pg/ml; and b) the level of fibronectin in the second sample is lower than about 400 mg/ml, and/or lower than about 350 mg/ml, and/or lower than about 300 mg/ml may be indicative of the subject having a vasculopathy as described herein or the subject being at risk for developing or increasing the rate of onset of a vasculopathy as described herein.

In another aspect of the present invention, there is provided a method of medical treatment comprising administering a therapeutically effective amount of a granzyme B inhibitor for treating a vasculopathy.

As used herein "vasculopathies" or "vasculopathy" refer to any vascular disease resulting from occlusive or aneurysmal processes of arteries or veins, of all sizes, which may occur almost anywhere in the body. For example, vasculopathies include, but are not limited to, atherosclerosis; aneurysm; and dissection. Accordingly, a subject being at risk for or having a vasculopathy may be characterized by a subject being at risk for or having atherosclerosis, aneurysm or dissection.

As used herein "Atherosclerosis" (or "Arteriosclerosis") is a disease in which plaque builds up on the inside of arteries. Atherosclerosis is characterized by the thickening of the arterial wall, usually at sites in the arterial tree where laminar flow is disrupted. This inflammatory vasculopathy is characterized by the excessive accumulation of lipids and modified lipids in the intima, medial damage, and the thickening and structural re-organization of the vessel wall. Physical forces, or the exposure to elevated levels of circulating low density lipoprotein (LDL) or free radicals caused by smoking, hypertension, or diabetes mellitus can cause endothelial dysfunction. These factors alter endothelial function by increasing the release of pro-inflammatory cytokines and vasoactive substances, which can result in interference with normal anti-thrombotic properties and permeable barrier functions, and increasing expression of cell-surface adhesion molecules. Atherosclerosis begins as a fatty streak consisting of atherogenic lipoproteins entering the intima and becoming modified. The increase of cell-surface adhesion molecules causes the recruitment and intravasation of leukocytes, monocytes and T-cells. Pro-inflammatory cytokines expressed within the developing lesion provide chemotactic stimulus to the adherent leukocytes, increasing their migration into the intima. Monocyte colony stimulating factor (M-CSF), which is also produced in the plaque, augments the expression of macrophage scavenger receptors to uptake modified lipids. Macrophages phagocytose this modified lipid in an unregulated manner, causing the formation of foam cells, which make up the fatty streak. Leukocytes, as well as resident vascular wall cells, secrete cytokines and growth factors that promote the migration and proliferation of smooth muscle cells (SMC). Vascular SMC (VSMC) may also release factors that degrade elastin and collagen in response to inflammatory stimulation, which allows the cells to migrate through the elastic lamina and collagenous matrix. VSMC proliferate and migrate from the media to the developing plaque in the intima, and contribute to the fatty streak development into an intermediate lesion by excessive extracellular matrix (ECM) secretion. This ECM increases the retention and aggregation of lipoproteins. Accordingly, administration of a GrB inhibitor would at this stage potentially increase ECM and therefore increase the retention and aggregation of lipoproteins. However, the present findings suggest that administration of a GrB inhibitor in the middle to late stages of plaque development would have a benefit.

As the plaque continues to grow, additional lymphocyte recruitment follows, and VSMC form a fibrotic cap under the endothelial layer. The fibrous cap eventually becomes thin and weak by a combination of an inhibition of collagen synthesis from VSMC and the expression of collagenases by foam cells. Eventually, a lesion can develop that is vulnerable to rupture, exposing thrombogenic material in the form of necrotic foam cells. The plaque may also grow without rupture, and may eventually obstruct blood flow. The formation of a thrombus which may block blood flow or the obstruction of a vessel from plaque formation can lead to ischemia of distal tissue.

A "dissection" (or arterial dissection) is a tear in the wall of the vessel intima and inner layer of the vessel media that allows blood to flow between the layers of the vessel wall and to split the vessel media apart. A dissection is a medical emergency and can quickly lead to death, even with optimal treatment. If for example the dissection is in the aorta and tears the aorta completely open (through all three layers) massive and rapid blood loss occurs. A tear causes the formation of a false lumen through the media, which is separated from the true lumen by an intimal flap. Medial necrosis or degeneration of aortic media, such as what is seen in aneurysms, is thought to be a prerequisite for dissection. Mechanical forces contributing to aortic dissection include flexion forces of the vessel at fixed sites, the radial impact of the pressure pulse, and the shear stress of the blood. Hypertension adds to a mechanical strain on the aortic wall and to the shearing forces exerting a longitudinal stress along the aortic wall. A combination of these factors results in an intimal tear and the propagation of dissection into the aortic media.

An "aneurysm" (or aneurism) as used herein may be a localized, blood-filled focal dilation of a blood vessel which may result from a weakening of the vessel wall, which can lead to a rupture of the vessel wall, excessive hemorrhaging, and death if not surgically repaired. Cerebral aneurysms, generally occur in arteries at the base of the brain in what is known as the circle of Willis and in the aorta. Aneurysms also commonly occur in the abdominal or thoracic aorta.

Plaque size and atherosclerosis, aneurysm, dissection severity may be determined by one or more of the following:

(a) Blood tests may be used to detect increased levels of cholesterol and blood sugar that may increase the risk of atherosclerosis.

(b) Doppler ultrasound may be used to measure blood pressure at various points along an arm or leg, which may assist in gauging the degree of any blockages, as well as the speed of blood flow through arteries.

(c) Ultrasound for echogenicity vessel plaque assessment (see Skjelland, et al. Atherosclerosis, 195:e142-e146 (2007)).

(d) Ankle-brachial index, may assist with diagnosis of atherosclerosis in the arteries of legs and feet. Furthermore, a comparison of the blood pressure at a subjects ankle with that at a subjects arm to produce an ankle-brachial index, whereby an abnormal difference may indicate peripheral vascular disease, which may be caused by atherosclerosis.

(e) Electrocardiogram (ECG) may record electrical signals as they travel through the heart and may often reveal evidence of a previous heart attack or one that's in progress. Furthermore, ECG may be carried out during exercise.

(f) Angiogram (with dye) allows for a view blood flow through the heart, brain, arms or legs, which can show narrow spots and blockages on the X-ray images.

(g) Other imaging tests may use ultrasound, a computerized tomography (CT) scanning or a magnetic resonance angiogram (MRA) to image the arteries with and without contrast, which may show hardening and narrowing of large arteries, as well as aneurysms and calcium deposits in the artery walls.

An inhibitor of granzyme B is a substance that will inhibit or slow down the cleavage of extracellular proteins by granzyme B. For example, a compound or composition that prevents granzyme B from cleaving fibronectin, elastin and/or fibrillin is a granzyme B inhibitor. In many cases, inhibitors are referred to as antagonists. Conversely, a substance that improves the ability of granzyme B to cleave extracellular proteins is called an agonist. For example, a compound or composition which would increase the rate at which granzyme B cleaves fibronectin, elastin and/or fibrillin is a granzyme B agonist.

A granzyme B inhibitor may be identified by contacting granzyme B with a test compound in order to form a primed granzyme B. A test compound is a substance, compound or composition that one wishes to identify as an inhibitor of granzyme B or not. A primed granzyme B is a granzyme B enzyme which may or may not have a test compound bound to it and has been in contact or mixed with a test compound.

In other words, a primed granzyme B is a granzyme B enzyme under conditions such that by adding an extracellular protein, such as fibronectin, elastin and/or fibrillin or a fluorescently labeled substrate containing the granzyme B preferred cleavage sequence (Z-sequences (AAD-AMC, IEPD, IETD)), a test compound may be identified as being an inhibitor or an antagonist of granzyme B or not. Once a primed granzyme B is formed, by contacting it with a predetermined amount of an extracellular protein, such as fibronectin, elastin and/or fibrillin, it is possible to identify whether or not a particular test compound is a granzyme B inhibitor or antagonist or not by measuring an amount of cleaved extracellular protein that accumulates over a predetermined period of time and comparing the amount of cleaved extracellular protein with a normal amount of cleaved extracellular protein. A normal amount of cleaved extracellular protein can be achieved by adding the same predetermined amount of the extracellular protein to granzyme B, i.e., unprimed granzyme B, and measuring the amount of cleaved extracellular protein that accumulates over the aforementioned predetermined period of time. The predetermined period of time may be any period of time that does not result in cleavage of all of the predetermined amount of the extracellular protein by unprimed granzyme B. A test compound is an inhibitor or antagonist of granzyme B if the amount of the cleaved extracellular protein is less than the normal amount of cleaved extracellular protein. If the amount of cleaved extracellular protein is the same as the normal amount of cleaved extracellular protein, then the test compound is not an inhibitor or antagonist of granzyme B. Alternatively, if the amount of cleaved extracellular protein is greater than the normal amount of cleaved extracellular protein, then the test compound is an agonist of granzyme B. Similar assays may be used to identify a rate of elastic fiber cleavage by granzyme B in the presence or absence of a particular inhibitor, antagonist or agonist.

Granzyme B inhibitors include any molecule that inhibits the GrB protein, either directly or indirectly, for example by up regulating endogenous inhibitors (e.g., PI9) and/or shutting down transcription of the GrB gene or translation of the GrB transcript. DNA/RNA can be used to inhibit the protein directly (aptamers) or the transcription/translation of GrB. Granzyme B inhibitors include, but are not limited to, peptides, antibodies (for example, polyclonal; monoclonal, fragments (F(ab')$_2$ and Fab)), small molecules, scFc, peptidomimetics, siRNA, antisense molecules (such as RNA and other nucleic acid molecules) etc. Furthermore, a GrB inhibitor may not be specific for GrB alone and may be a broad spectrum inhibitor of granzymes (as a family) or an inhibitor of serine protease.

Many granzyme B inhibitors are known to a person of skill in the art and are, for example, described in international patent application published under WO 03/065987 and United States patent application published under US 2003/0148511; Willoughby C A. et al. *Bioorg. Med. Chem. Lett.* 12:2197-2200 (2002); Hill G E. et al. *J. Thorac. Cardiovasc. Surg.* 110:1658-1662 (1995); Sun J. et al. *J. Biol. Chem.* 271:27802-27809 (1996); Sun J. et al. *J. Biol. Chem.* 272: 15434-15441 (1997); Bird et al. *Mol. Cell. Biol.* 18, 6387-6398 (1998); Kam et al. *Biochim. Biophys. Acta* 1477:307:23 (2000); and Bio-x-IEPDP-(OPh)$_2$ as described in Mahrus S. and Craik C S. *Chemistry & Biology* 12:567-577 (2005). Antisense oligonucleotides directed against granzyme B have been designed and manufactured by Biognostik (Euromedex, Mundolshei, France) and are described in Hernandez-Pigeon, et al., *J. Biol. Chem.* 281: 13525-13532 (2006) and Bruno, et al., *Blood*, 96: 1914-1920 (2000). Further examples of granzyme B inhibitors are: Z-AAD-CMK (IUPAC name: 5-chloro-4-oxo-2-[2-[2-(phenylmethoxycarbonylamino) propanoylamino]propanoylamino]pentanoic acid) MF: $C_{19}H_{24}ClN_3O_7$ CID: 16760474; Ac-IEPD-CHO; Granzyme B Inhibitor IV or Caspase-8 inhibitor III (IUPAC: (4S)-4-[[(2S)-2-acetamido-4-methylpentanoyl]amino]-5-[2-[[(2S)-4-hydroxy-1,4-dioxobutan-2-yl]carbamoyl]pyrrolidin-1-yl]-5-oxopentanoic acid) MF: $C_{22}H_{34}N_4O_9$ CID: 16760476; and Ac-IETD-CHO; Caspase-8 Inhibitor 1 or Granzyme B Inhibitor II (IUPAC: (4S)-4-[[(2S,3S)-2-acetamido-3-methylpentanoyl]amino]-5-[[(2S,3 S)-3-hydroxy-1-[[(2S)-4-hydroxy-1,4-dioxobutan-2-yl]amino]-1-oxobutan-2-yl] amino]-5-oxopentanoic acid) MF: $C_{21}H_{34}N_4O_{10}$ CID: 16760475. Methods of identifying a granzyme B inhibitor are described elsewhere in this application.

The granzyme B inhibitor may be formulated for a variety of different suitable routes of administration, such as inhalation, topical, parenteral, enteral and others. Furthermore, a granzyme B inhibitor may be applied topically to a plaque, dissection, or aneurysm site. Alternatively, the granzyme B inhibitor may be formulated for application to the surface of a device (for example, as a coating on a stent, clip, catheter, coil etc.).

In another aspect of the present invention, there is provided use of a granzyme B inhibitor for treatment of one or more of: atherosclerosis; aneurysm; and dissection. The dissection may be an aortic dissection and the aneurysm may be an aortic aneurysm.

Many molecules, compounds and compositions of this invention or for use in this invention are generally water soluble and may be formed as salts. In such cases, pharmaceutical compositions in accordance with this invention may comprise a salt of such a compound, preferably a physiologically acceptable salt, which are known in the art. Pharmaceutical preparations will typically comprise one or more carriers acceptable for the mode of administration of the preparation, be it by injection, inhalation, topical administration, lavage, or other modes suitable for the selected treatment. Suitable carriers are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, 20$^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel. Formulations of antisense nucleic acid molecules are also known to a person of skill in the art. Isis pharmaceuticals is a company that has developed several antisense formulations, including Vitravene™. Such formulations may be used with antisense nucleic acid molecules that are inhibitors of granzyme B.

Compounds or pharmaceutical compositions in accordance with this invention or for use in this invention may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced extracellular matrix protein cleavage, reduced levels of granzyme B activity, improved inflammation state, improved air flow in the lungs, improved blood flow, and/or a delay or reduction in the severity of the onset of a vasculopathy as described herein. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as reduced extracellular matrix protein cleavage, reduced levels of granzyme B activity, improved improved blood flow, reduced plaque formation, improved plaque stability, improved vessel elasticity, maintenance of vessel wall thickness, and maintenance of vessel wall elastin and fibrillin-1 content as described herein. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In general, compounds of the invention should be used without causing substantial toxicity. Toxicity of the compounds of the invention can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be necessary to administer substantial excesses of the compositions.

As used herein, a "subject" or "normal subject" may be a human, non-human primate, or a mammal, or a rat, mouse, cow, horse, pig, sheep, goat, dog, cat, etc. The subject may be suspected of having or at risk for having a vasculopathy as described herein. Some diagnostic methods for a vasculopathy as described herein and the clinical delineation of diagnoses of a vasculopathy as described herein are known to those of ordinary skill in the art.

Furthermore, subjects may be tested for GrB levels to determine their risk of a poor outcome from their vasculopathy. A poor outcome may be the dissection or rupture of a vessel wall or a plaque rupture or decreased stability of one or more plaques. To evaluate a subjects risk, blood samples (7.5 ml) may be collected from normal subjects having or suspected of having a vasculopathy using a purple top EDTA vacutainer tube (BD™) Following collection, the tube may be inverted 5 times for thorough mixing. The tubes may then be then centrifuged for 11 min at 276×g (Beckman Coulter™). Following centrifugation, the tubes should be separated into 3 distinct layers: a bottom layer of mostly red blood cells, a thin film layer of white blood cells (buffy coat) and a top layer of plasma. Using a sterile transfer pipette, the top layer of plasma down to about 1 mm from the red blood cells may be removed, with caution so that you are careful not to aspirate the buffy coat, and the plasma can then be placed into a labeled orange top cryotube. The samples may be stored immediately at −80° C. until plasma analysis is performed.

For plasma analysis, human Granzyme B ELISA kits are available from Bender Medsystems™ (catalog number: BMS2027). The kits comprise enzyme-linked immunosorbent assay for quantitative detection of human granzyme B. The reagents may be prepared as per the kit's protocols: a) Wash Buffer; b) Dilution Buffer; c) Biotin-Conjugate; d) Granzyme standards; e) Streptavidin-HRP; and f) Colour-giving reagents: Blue-Dye, Green-Dye, Red-Dye. The assays may be performed as per the kit's protocols and the calculation of the results may also be performed as per the kit's protocols.

Antibody Production

One methodology is to detect the presence of GrB or elastin specific peptides or proteins. GrB or elastin specific peptides or proteins may also include degradation products thereof These peptides or proteins may be detected by isolating proteinaceous material from a biological sample and determining the sequence of peptides or proteins so isolated and comparing to the known sequence of GrB or elastin proteins. Preferably, such detecting will make use of an intermediate agent such as an antibody specific for the GrB or elastin peptide or protein as known in the art.

Antibodies to GrB or elastin peptides or proteins may be prepared by a variety of known methods. Such antibodies may be polyclonal, monoclonal, or may be fragments of antibodies.

For the production of antibodies, various hosts including goats, rabbits, rats, mice, humans, and others, may be immunized by injection with a GrB or elastin peptide or protein fragment which has immunogenic properties. Depending on the host species, various adjuvants may be used to increase immunological response. Such adjuvants include, but are not limited to, Freund's, mineral gels such as aluminum hydroxide, and surface active X substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that GrB or elastin peptides, fragments, or oligopeptides used to induce antibodies have an amino acid sequence consisting of at least five amino acids, and more preferably at least 10 amino acids. It is also preferable that they are identical to a portion of the amino acid sequence of the natural protein, and they may contain the entire amino acid sequence of the GrB or elastin peptide or protein. Short stretches of GrB or elastin amino acids may be fused with those of another protein such as keyhole limpet hemocyanin and antibody produced against the chimeric molecule.

Peptides corresponding to a GrB or elastin amino acid sequence may be synthesized using methods known in the art, including the recombinant techniques disclosed in the examples below. Such peptides may also be made to incorporate a N-terminal cysteine to facilitate conjugation to other molecules (e.g. to enhance immunogenicity) with such conjugation being mediated by an agent such as m-maleimido-benzoyl-N-hydroxy-succinimide ester (MBS). Antibodies that specifically react with the peptide may be purified from the antisera by affinity chromatography, for example by using Cellulofine (Seikagaku Corporation) conjugated with the peptide. The resulting antibodies may be tested by immunoblotting.

Monoclonal antibodies to GrB or elastin peptides or proteins or anti-idiotypic monoclonal antibodies may be prepared using any technique, which provide for the production of antibody molecules by continuous cell lines in culture. These include, but are not limited to, the hybridoma technique, the human B-cell hybridoma technique, and the EBV-hybridoma technique (Kohler, G. et al. (1975) *Nature* 256: 495-497; Kozbor, D. et al. (1985) J. Immunol. Methods 81:31-42; Cote, R. J. et al. (1983) Proc. Natl. Acad. Sci. 80:2026-2030; Cole, S. P. et al. (1984) Mol. Cell Biol. 62:109-120).

One process for obtaining the hybridomas of this invention involves starting from spleen cells of an animal, e.g. mouse or rat, previously immunized in vivo or from spleen cells of such animals previously immunized in vitro with an antigen and fusing the immunized cells with myeloma cells under hybridoma-forming conditions; and selecting those hybridomas which secrete the monoclonal antibodies which are capable of specifically recognizing the GrB or elastin peptide or protein.

Selected hybridomas are cultured in appropriate culture medium; and then the secreted monoclonal antibodies are recovered; or alternatively the selected hybridoma is implanted into the peritoneum of a mouse and, when ascites has been produced in the animal; the monoclonal antibodies formed from the ascites are recovered. Monoclonal antibodies of the invention may be prepared by conventional in vitro techniques such as the culturing of immobilized cells using e.g. hollow fibers or microcapsules or such as the culturing of cells in homogeneous suspension using e.g. airlift reactors or stirred bioreactors.

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851-6855; Neuberger, M. S. et al. (1984) Nature 312:604-608; Takeda, S. et al. (1985) Nature 314:452-454). Alternatively, techniques described for the production of single chain antibodies may be adapted, using methods known in the art, to produce GrB or elastin-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120-3). Such single chain antibodies may also be used for production of anti-idiotypic antibodies for use in this invention.

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833-3837; Winter, G. et al. (1991) Nature 349:293-299).

Antibody fragments which contain specific binding sites specific for GrB or elastin peptides or proteins or for anti-GrB or elastin antibodies may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Ruse, W. D. et al. (1989) Science 254:1275-1281). Such fragments when specific for anti-GrB or elastin antibodies may be used for production of anti-idiotypic antibodies or fragments thereof.

Monoclonal antibodies of this invention may be "chimeric", an example of which is an animal antigen-binding variable domain coupled to a human constant domain (Cabilly et al., U.S. Pat. No. 4,816,567; Morrison, S. L. et al., Proc. Natl. Acad. Sci. USA 81:6851-6855 (1984); Boulianne, G. L. et al., Nature 312:643-646 (1984); Neuberger, M. S. et al., Nature 314:268-270 (1985)). The term "chimeric" antibody describes a polypeptide comprising at least the antigen binding portion of an antibody molecule linked to at least part of another protein such as an immunoglobulin constant domain. However, antibodies of this invention may be conjugated to a variety of moieties including labeling moieties.

Various immunoassays may be used for screening to identify antibodies having a desired specificity. Numerous protocols for competitive binding or immunoradiometric assays using either polyclonal or monoclonal antibodies with established specificities are well known in the art. Such immunoassays typically involve the measurement of complex formation between a GrB or elastin antigen and its specific antibody. Monoclonal-based immunoassays utilizing monoclonal antibodies reactive to at least two non-interfering epitopes are preferred, but competitive binding assays may also be employed (Maddox, D. E. et al. (1983; J. Exp. Med. 158: 1211-1216).

Antibody Assay Methods

One of the most important utilities of the antibodies and proteins/peptides of the invention is for diagnostic purposes, in particular in assays to detect of quantify the presence of GrB or elastin antibodies or antigen (GrB or elastin protein or peptide) in a sample. In the following, such assays, in particular ELISAS (enzyme-linked immunosorbent assays) and Western blots can be used to detect GrB or elastin proteins or peptides in samples. Numerous immunoassays are known in the art (Methods in Cell Biology, Vol. 37: Antibodies in Cell Biology, Asai, ed., Academic Press, Inc., New York (1993); and Basic and Clinical Immunology, $7^{th}$ ed., a Stites & Terr, eds., (1991)).

A preferred method for detecting GrB or elastin proteins is the ELISA, in which an antibody typically is bound to an enzyme, such as peroxidase or phosphatase, which can produce colored reaction products from an appropriate buffer. Thus, it utilizes a tagged antigen molecule of known quantity to determine an unlabelled antigen of unknown quantity. Preferably, a GrB or elastin protein according to the invention, or a suitable functional fragment thereof, is used coupled to a conventional tag, such as His6.

Thus, in an ELISA format according to the invention, polypeptides or proteins specific for GrB or elastin are detected and/or quantified, preferably in a biological sample. The sample may be any sample of biological tissue or fluid, such as blood. The sample is pretreated as necessary by dilution in a suitable buffer solution or concentrated, if desired. Any number of standard aqueous buffer solutions may be used, such as Tris or the like, at physiological pH. Samples are incubated with an excess of the protein according to the invention as antigen. After rinsing to remove any unbound antigen, the amount of bound antigen is quantitated by adding a solution of enzyme-conjugated antibody that binds to constant domains of antibodies in the sample. Excess conjugated antibody is rinsed away and the activity of the bound enzyme is determined by adding the substrate to the reaction and measuring the formation of products. As the products of the reactions used in ELISA procedures are colored, the amount of product formed can readily be determined by the intensity of the colour that has developed using a spectrophotometer. The activity of the bound enzyme is proportional to the amount of antigen-binding antibody in the sample; therefore, the original concentration of such antibodies can be estimated from a series of control assays employing known concentrations of specific antigens. Similarly, antibodies to GrB or elastin can be detected in a biological sample using bound antigen (GrB or elastin protein or peptide).

As an alternative method for detecting GrB or elastin proteins Western blots can be utilized taking advantage of the GrB or elastin specific antibodies described above. Biologic samples containing proteins can be assayed by fractionation on polyacrylamide gels under denaturing conditions. Alternatively, tris tricine polyacrylamide gel electrophoresis can be used for improved separation of small peptides in the range from 1 to 100 kDa (Schagger H. and von Jagow G. 01987) Analytical Biochemistry 166:368-379 and Klafki H.-W. et al. (1996) Analytical Biochemistry 237:24-29.). The proteins separated in the gels can then be transferred to a membrane using a variety of methods known in the art. Membranes can then be probed using GrB or elastin specific antibodies in a Western blot to identify the proteins of interest in the biological sample preparations. Numerous Western blotting methods are known in the art (ECL Western blotting protocol—Amersham; Hsu S M. Methods Enzymol. (1990) 184:357-63; Leong M M. and Fox G R. Methods Enzymol. (1990) 184: 442-51).

Western Blotting

As an alternative method for detecting GrB or elastin proteins or peptides Western blots can be utilized taking advantage of the GrB or elastin specific antibodies described above. Biologic samples containing proteins can be assayed by fractionation on polyacrylamide gels under denaturing conditions. Alternatively, tris tricine polyacrylamide gel electrophoresis can be used for improved separation of small peptides in the range from 1 to 100 kDa (Schagger H. and von Jagow G. (1987) Analytical Biochemistry 166:368-379 and Klafki H.-W. et al. (1996) Analytical Biochemistry 237:24-29.). The proteins separated in the gels can then be transferred to a membrane using a variety of methods known in the art. Membranes can then be probed using GrB or elastin specific antibodies in a Western blot to identify the proteins or peptides or degradation products thereof of interest in the biological sample preparations. Numerous Western blotting methods are known in the art (ECL Western blotting protocol—Amersham; Hsu S M. Methods Enzymol. (1990) 184: 357-63; Leong M M. and Fox G R. Methods Enzymol. (1990) 184:442-51).

Alternatively, GrA or GrB enzyme-linked immunosorbent spot (ELISPOT—Czerkinsky C. et al. (1983) J Immunol Methods 65 (1-2): 109-21), dot blots or other proteomic approaches known in the art.

Various alternative embodiments and examples of the invention are described herein. These embodiments and examples are illustrative and should not be construed as limiting the scope of the invention.

EXAMPLES

Methods and Materials

Animals

All animal protocols were approved by the University of British Columbia (UBC) Animal Care Committee. C57B1/6 mice, C57B1/6-ApoE−/− and C57B1/6-GrB−/− mice were obtained from Jackson Laboratories (Bar Harbor, Me.) (PIEDRAHITA et al. 1992. *Proc Natl. Acad Sci* 89: 4471-4475; HEUSEL et al 1994 *Cell* 76:977-987). The C57B1/6-ApoE−/− x GrB−/− double knockout (ApoE/GrB-DKO) mice were generated by crossing the C57B1/6-ApoE−/− and C57B1/6-GrB−/− mouse strains. Genotyping of the mice was performed using primers and PCR reactions designed for genotyping these lines from Jackson laboratories (GrB primers: 5'-TGAAG ATCCT CCTGC TACTG C-3' and 5'-TCCTG AGAAA GACCT CTGCC-3'; ApoE primers: 5'-GCCTA GCCGA GGGAG AGCCG-3' and 5'-TGTGA CTTGG GAGCT CTGCA GC-3'). The pups were weaned at 3 weeks of age and then maintained on a 12-hour day and night cycle with food and water provided ad libitum. At 6-8 weeks of age, mice for examples 1-7 (7A) were maintained on either regular chow or a Western high fat diet (Harlan Teklad) for 30 weeks and were sacrificed to collect blood and tissues. At 3 months of age, the mice for examples 8-14 were randomly assigned to receive either 28 days of angII infusion, or saline infusion from a subcutaneous 1004 model ALZET® mini osmotic pump.

ApoE-KO Model of Angiotensin-II-Induced AAA

To induce aneurysms, we used the well-characterized angII osmotic minipump method (Daugherty A. et al. J Clin Invest 105, 1605-12 (2000)). ALZET™ osmotic pumps (DURECT Corporation, Cupertino, Calif.) are miniature, implantable pumps commonly used for research in mice and rats. These infusion pumps continuously deliver drugs and other test agents at controlled rates from one day to four weeks without the need for external connections or frequent handling. ALZET™ pumps operate by osmotic displacement. An empty reservoir within the core of the pump is filled with the drug solution to be delivered. Due to the presence of a high concentration of salt in a chamber surrounding the reservoir, water enters the pump through its outer surface. This entry of water increases the volume in the salt chamber, causing compression of the flexible reservoir and delivery of the drug solution into the animal.

Mice were weighed immediately before calculating doses, and the mean weight of mice per group was used. Since mice on a regular diet gain 0.5 g of weight per week, the drug dose was calculated based on the projected mid weight of the experiment (so mice were slightly overdosed for the first two weeks and under-dosed for the final two weeks). The dose was calculated based on the pump fill volume, mean pumping rate, and the midpoint weight of the mice to achieve a value of 1.44 mg/kg/day, (equivalent to 1000 ng/min/kg). To ensure accurate filling, pumps were weighed before and after filling, and a value of 1 mg equal to 1 μL was used when assessing fill volume. AngII was obtained from Sigma in 5 mg aliquots, and stored at −20° C. until use. Fresh angII was diluted in saline for each experiment. All pumps and solutions were worked with under sterile conditions. After filling of the pump with angII or vehicle control, they were stored in sterile tissue culture tubes, containing enough saline to completely cover the pump. All test tubes were placed in the incubator at 37° C. for 24 hours prior to implantation. Normally the pumps should incubate for 48 hours before they will begin to release angII at the proper flow rates and doses. However, this 24 hour incubation allowed the pumps to partially prime. They should not begin releasing angII at full dose for an additional 24 hours after implantation. This will allow the mice 1 day to recover from the surgery of implantation, prior to the potential stress of angII infusion.

On day 1, mice were brought into the GEM micro-procedure room Animals were anesthetised with gaseous anaesthetic at a flow rate of 1.5 L per minute of oxygen with 2.5% of isoflurane delivered via a Baines system using a calibrated tabletop anaesthetic machine, administered from a rodent nose cone. Depth of anaesthesia was monitored by toe pinch response and breathing. Eyes were protected using ocular lubricant. The back of the mouse was shaved, and the legs were taped down. The back of the mouse was then sterilized with 70% ethanol, followed by iodine. The mouse was then moved to the surgical table, so that the dissecting microscope could be utilised.

Under sterile conditions, a lateral incision was made below the scapula, and the skin was blunt dissected from the subcutaneous layer, making a hole large enough to fit the minipump. The minipump was inserted with the flow regulator angled towards the head. Incisions were closed with 2-4 dissolving discontinuous sutures. Isoflurane was then shut off, allowing the mouse to breathe pure oxygen, and a dose of buprenorphine was administered for pain relief After 1 hour, when the mice had recovered from anaesthesia, they were moved back to the animal holding room. The mice were monitored daily for the remainder of the experiment.

At day 28, tissues from the surviving mice were collected. Blood was collected by cardiac puncture following $CO_2$ euthanization. The mouse was placed on ice, the chest is opened, the right atrium cut, and a needle is placed in the left ventricle. Saline, and then 4% para-formaldehyde, was perfused at a constant pressure of 100 mm Hg using a pressurized tubing system until no blood is observed exiting the incision in the right atria. The heart, aorta to the iliac bifurcation, and kidneys were dissected from the mouse and photographed. At this point, a gross description of the aorta is made. In the case of the mice that were found deceased, tissue perfusion was not an option. In these cases, the aorta and heart were collected without perfusion. Due to autolysis, some tissue was difficult to dissect and was lost. The tissue was stored in fresh 4% para-formaldehyde overnight, and photographed again before being sectioned and embedded.

Tissue and Blood Collection

Animals were overdosed with 2.5% Avertin™ (Sigma™) and perfusion fixed with four mL of 4% formalin (Sigma™) at a flow rate of 2 mL/min. The hearts were then rapidly removed, and aortic root sections were optimal cutting temperature (OCT)-embedded. Skin samples taken from the back were either OCT-embedded (Tissue-Tek™) or immersion-fixed in 10% formalin for 24 h before being embedded in paraffin. Blood extracted by cardiac puncture was collected in EDTA microvette tubes (Sarstedt™), spun at 10,000×g for 7 minutes at 4° C., and the separated serum stored at −80° C. until required for analysis.

Tissue Fixation, Excision and Processing
Aortic Roots

The upper half of the heart (containing the atria and aortic arch) was frozen in optimum cutting temperature embedding medium (OCT) (Cryomatrix, Shandan) for serial cryosectioning covering 10 nm of the root. From each heart 10-20 sections were obtained. Sections were stained with Oil red O (ORO), Hematoxylin and eosin (H&E) and Movat's Pentachrome (Movat's) stains to examine the presence of atherosclerotic lesions present in the aortic root (see below for protocol). The slides were then viewed under a light microscope. ImageProPlus™ (MediaCybernetics, Silver Spring, Md.) was used to trace and quantify the atherosclerotic lesions, as well as the lumen area and valve area of each sample.

Atherosclerotic lesions were expressed as the cross-section area of the lesions, as well as the ratio of lesion to valve cross sectional area, and lesion to lumen area.

Abdominal and Thoracic Aortic Sections

Sections were isolated from the descending aorta immediately above the diaphragm, and the thoracoabdominal aorta immediately above the renal arteries. These sections were embedded and frozen in OCT, and serially cryosectioned into 10 μm specimens.

Histological Stains
Hematoxylin & Eosin

Tissue sections were washed in two, 5 min changes of water to remove OCT. Slides were then immersed in hematoxylin for 5 min, removed, washed in $dH_2O$ for 1 min, differentiated in 1% acid alcohol rapidly (5-10 sec), washed in $dH_2O$ for 1 min, and then immersed in lithium chloride for 30 sec. The tissue was then washed in $dH_2O$ for 1 min and immersed in 70% isopropyl alcohol for 30 sec before staining with eosin. Slides were immersed in 1% eosin in 80% alcohol for 30 sec, drained, air-dried overnight, and immersed in xylene for automatic coverslipping. All slides were examined under light microscopy and photomicrographs obtained on a Spot™ digital camera. The exposure was automatically calculated subsequent to white balancing.

Movat's Pentachrome

Tissue sections were washed in two, 5 min changes of water to remove OCT. Slides were oxidized by saturation in aqueous picric acid for 10 min at room temperature, washed in running water until colourless, rinsed in $dH_2O$ and then rapidly immersed in 3% acetic acid. Slides were then immediately immersed in Alcian Blue (1 g Alcian Blue, 3 mL glacial acetic acid in 100 mL $dH_2O$) for 30 min, rinsed in 3% acetic acid, and washed in warm running tap water for 10 min. After rinsing in $dH_2O$, slides were immersed in Verhoeffs stain for 45 min, then rinsed and soaked in warm tap water for 5 min. Tissue sections were then washed in $dH_2O$, immersed in Biebrich Scarlet-Acid Fuchsin (0.8 g Biebrich Scarlet, 0.6 g Acid Fuchsin, 1.6 g Phosphotungstic acid in 140 mL $dH_2O$) for 10 min, rinsed in $dH_2O$, and the colour differentiated in 5% phosphotungstic acid for 2 min. Finally, the slides were rinsed with $dH_2O$ and de-hydrated in 3 changes of 100% ethanol before staining in alcoholic saffron (6 g saffron in 100 mL ethanol) for 10 min at 60° C. (modified from Movat H. Z. AMA Arch Pathol, 60:289-95 (1955)) The tissue sections were set to air dry overnight, and then immersed in xylene before coverslipping using an automatic machine.

AT1 and Fibrillin-1 Staining

Tissue sections were washed in two, 5 min changes of water to remove OCT. Heat-based antigen retrieval was performed by boiling slides for 15 min in citrate buffer (pH 6.0) followed by 30 min of cooling in order to unmask antigenic epitopes that are modified by formalin-fixation. Slides were then washed in Phosphate Buffered Saline (PBS) twice, each time for 5 minutes. Slides were then quenched in 3% hydrogen peroxide, and washed in 3 changes of PBS. Slides were blocked with 10% normal goat serum in PBS for 30 min at room temperature. Blocking serum was removed, and 10% normal goat serum with either rabbit anti-fibrillin-1 (Dako; Carpinteria, Calif., USA), or rabbit anti-AT1 (Santa Cruz™; Santa Cruz, Calif., USA) overnight in a humidified chamber at 4° C. The primary antibody was removed, and the slides washed two times in PBS for 5 min in each wash at room temperature before incubation in a 1:350 dilution of biotin goat anti-rabbit in 5% normal goat serum for 30 minutes in chamber. The secondary antibody was then removed, the slides washed in PBS (pH 7.4) three times for 5 min in each wash. Prepared ABC reagent (VECTASTAIN™ ABC (Horseradish Peroxidase) kit, Burlingame, Calif.) was added to each section, and incubated for 30 min at room temperature. Slides were then washed in two changes of PBS with 0.1% tween (PBST) for 5 min each wash, and then one time in PBS for 5 min. To visualize staining Nova-red solution was incubated for 5-6 min, and following incubation slides were immediately washed in water. Slides were then counter-stained with hematoxylin for 1 min and washed in water. The tissue sections were set to air dry over night, and then immersed in xylene before coverslipping using an automatic machine.

ApopTag Peroxidase In Situ Apoptosis Detection Staining

ApopTag™ staining on OCT-embedded sections was utilized to assess DNA fragmentation and was carried out as per the manufacturer's instructions (Chemicon Internatural, Inc.). Slides were washed in water to remove OCT in the same manner as described above for immunohistochemistry. Slides were then washed twice in PBS for 5 min in each wash and incubated with 20 µg/mL proteinase K for 20 min at room temperature to permeabilize the tissue and to digest DNA-associated proteins. Slides were washed three times in PBS (for 5 min in each wash and residual peroxidase activity in tissues quenched with the addition of 3% $H_2O_2$ for 15 min at room temperature. After washing three times in PBS, tissue sections were incubated in equilibration buffer for at least 10 sec and then with TdT enzyme in the presence of digoxigenin UTP for 1 h at 37° C. TdT enzyme was then inactivated by incubation in Stop Buffer for 10 min. After washing the slides three times in PBS, anti-digoxigenin antibody conjugated to HRP was added for 30 min at room temperature to detect the DNA strand breaks that have been labelled with biotinylated UTP by TdT. Slides were then washed three times in PBS and staining was visualized by incubating slides in DAB for 5-10 min. Hematoxylin was used as a nuclear counterstain before coverslipping and microscopic examination of the stained sections. Photomicrographs were obtained as described above for immunohistochemistry.

Immunofluorescence

Immunofluorescence was performed on OCT-embedded frozen sections. Briefly, sections were fixed with acetone for 10 min. Background staining was blocked by incubation of sections with Dako protein block (Dako Cytomation™) for 20 minutes then incubation in 10% donkey serum for 1 hour. Sections were incubated in goat anti-granzyme B (Santa Cruz™, 1:50) and rat anti-mouse macrophage/monocyte (Chemicon™, 1:50) at 4° C. overnight, followed by incubation in donkey anti-goat IgG (Alexa Fluor™ 594, 1:500) and donkey anti-rat IgG (Alexa Fluor™ 488,1:500) for 30 min at room temperature in the dark. Slides were mounted with VECTASHIELD™ Hard-set mounting medium with 4'-6-Diamidino-2-phenylindole or DAPI (Vector Laboratories™, Burlingame, Calif.). Confocal microscopy was performed using a Leica AOBS™ SP2 confocal microscope.

Histological Assessment and Quantitation

Serial 10 µm sections of the aortic roots isolated as described were stained with hematoxylin & eosin (H&E), Movat's pentachrome, elastic van Gieson, or Oil Red O (ORO). ImageProPlus™ (MediaCybernetics™, Silver Spring, Md.) was used to quantify the lesion area per lumen cross section in ten to twenty sections from each mouse that survived to the 28 day endpoint, which were then averaged to provide mean lesion area per mouse. To calculate aortic lumen area and medial thickness, the internal and external elastic lamina from Movat's pentachrome stained sections were traced with ImageProPlus™. The maximum lumen area was calculated using the internal elastic lamina perimeter. The medial thickness was calculated by subtracting the maximum area calculated from the external elastic lamina from the maximum area calculated from the internal elastic area, and then dividing by internal elastic lamina perimeter value.

Human Tissue Collection. Human AAA were obtained in accordance with the ethical protocols at the Karolinska Hospital, Sweden. Elastic Van Gieson, and immunohistochemistry for GrB was performed on formalin-fixed, paraffin-embedded sections (Choy J C. et al. Mod Pathol 16:460-470 (2003)). Briefly, sections were de-paraffinized and rehydrated in xylene and decreasing concentrations of ethanol. Antigen retrieval was performed by boiling slides in citrate buffer (pH 6.0) for 15 minutes, and cooling on the bench top. For immunohistochemistry, background staining was blocked by incubation of sections in 10% goat serum for 30 minutes. Sections were incubated in a 1:100 dilution of either rabbit anti-GrB overnight, followed by incubation in the goat IgG secondary Ab for 1 hour. Staining was visualized with the chromagen Vector Red™, which possesses both colorimetric and fluorescent properties (Vector Laboratories™, Burlingame, Calif.), and nuclei were counter-stained with hematoxylin.

Statistics

An ANOVA test was performed to determine statistical differences between multiple groups. Statistical differences between two groups were determined using a Student's t-test. For both tests, a p value (alpha error) of 0.05 or less was considered significant.

Example 1

ApoE/Granzyme B Double Knock-Out Mice

Figure 4:
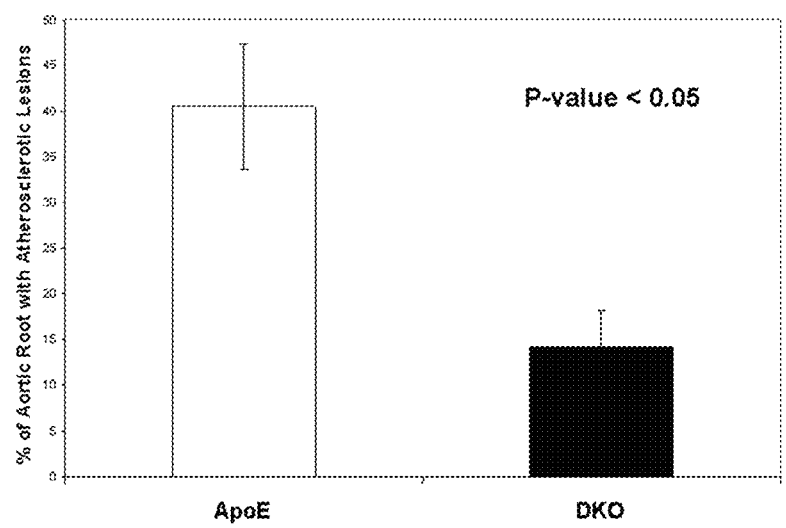
FIG. 4 Shows the percentage area of the aortic root in ApoE KO (white bar) and ApoE/GrB DKO (black bar) mice fed a Western diet. N=2 for the DKO mice, N=4 for the ApoE KO mice. Values for each section was calculated (sum of the plaque area)/(total aortic root area)*100%. For each animal, 3-7 sections of aortic roots were analyzed for % lesion area and averaged.
Figure 5:
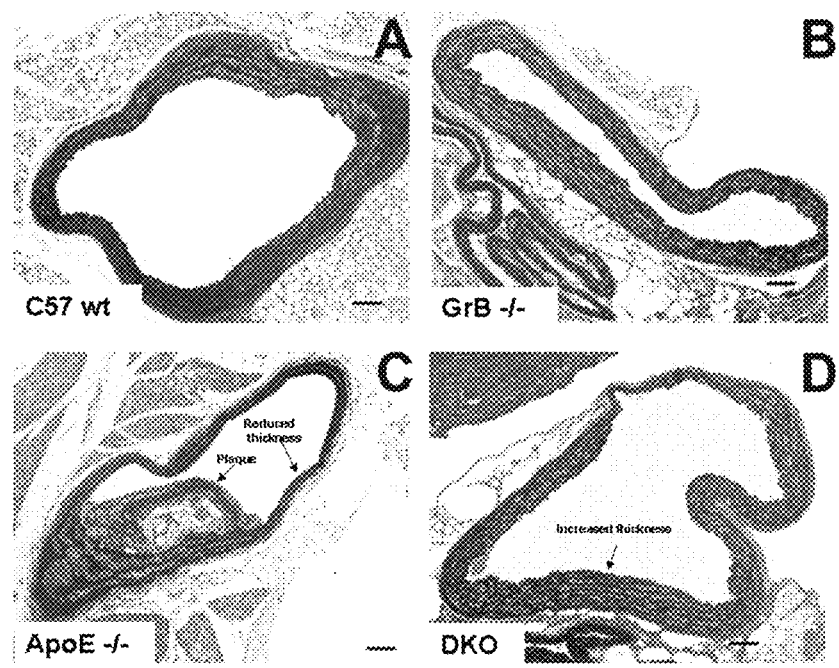
FIG. 5 Representative artery sections from mice fed a Western diet for 30 weeks. (A) C57 WT, (B) GrB−/−, (C) ApoE−/−, (D) ApoE/GrB-DKO.

Four groups of mice consisting of (1) C57Bl/6 wild-type, (2) C57/ApoE−/− (ApoE-KO), (3) C57/GrB−/− (GrB-KO), and (4) C57 GrB/ApoE-DKO were fed a normal chow or high fat 'Western' diet (21% fat, 0.2% cholesterol) for 30 weeks. No obvious phenotypic differences were observed in these mice during the first 3 months. Mice were sacrificed and tissues harvested at 30 weeks of age (ApoE KO mice on the Western diet are sacrificed around this age for humane reasons). As reported in the literature, the ApoE-KO mice had developed severe skin xanthomatosis, hair loss, hair discoloration and numerous atherosclerotic lesions. Surprisingly, the GrB/ApoE-DKO mice demonstrated a significant reduction in both frequency and size of atherosclerotic lesions (FIG. 4). Atherosclerotic lesions in the ApoE/GrB DKO mice decreased in size to less than 15% of the aortic root area, from more than 40% in the ApoE KO mice fed a Western diet.

Figure 2:
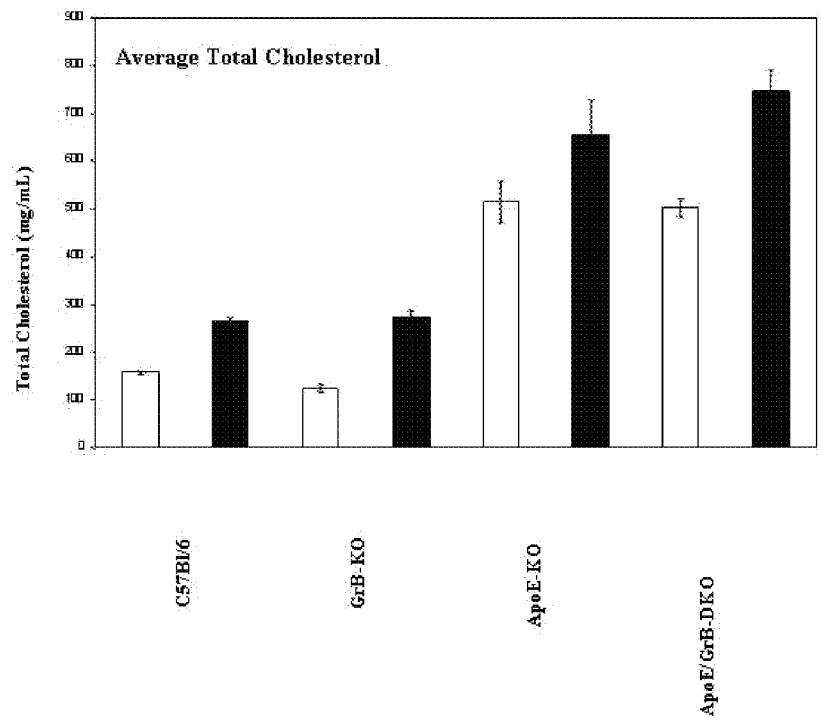
FIG. 2 is a bar graph showing the average total cholesterol in the plasma of C57/B1/6, GrB KO, ApoE KO or ApoE/GrB DKO mice. White bars represent mice fed a normal chow diet; black bars represent mice fed a Western diet. N=3 for each group. Total cholesterol (mg/ml) is the Y-axis.
Figure 3:
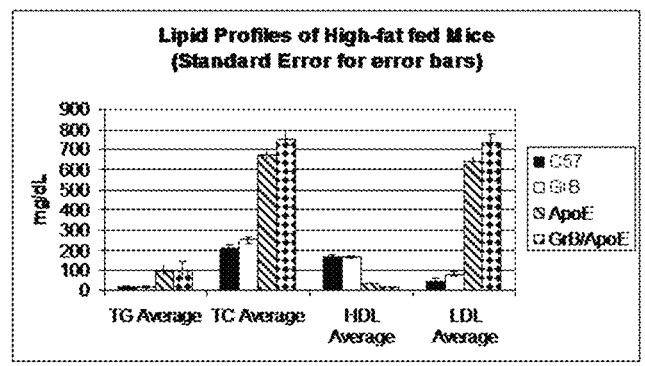
FIG. 3 is a bar graph showing the plasma lipid profiles of C57/B1/6 (solid bar), GrB KO (white bar), ApoE KO (hatched bar) or ApoE/GrB DKO (checked bar) mice on a Western diet. TG average—average triglycerides; TC average—total cholesterol average; HDL—high density lipoprotein; LDL—low density lipoprotein. N=3 for each group.

Interestingly, this difference in atherosclerotic lesions is not due to a change in blood cholesterol or lipoprotein levels, as there is no difference between the ApoE KO and the ApoE/GrB DKO mice (FIGS. 1 & 2)—both total cholesterol and LDL-C plasma concentrations are the same. No significant differences in HDL, LDL and triglycerides are observed between ApoE KO (hatched bars) and ApoE/GrB DKO (checked bars) mice fed a Western diet (FIG. 3). Removal of granzyme B activity alone (white bars) does not have a significant effect on the blood lipid profiles compared to the C57/BL6 (black bar).

ApoE KO mice exhibit signs of premature aging, necessitating sacrifice by about 30 weeks (6-7 months) of age, however the ApoE/GrB DKO mice remain healthy and vigorous beyond 12 months of age, with no visible signs of aging or illness. This was surprising, as no support or indication of a role for GrB in longevity has been previously identified in the literature.

Example 2

Elastin and Granzyme B Distribution in Aortic Sections

Co-localization of granzyme B and macrophages in the lesions of the aortic roots were performed and imaged by confocal microscopy. The ApoE-KO (ApoE−/−) lesions showed both granzyme B and macrophage staining, with co-localization of both at specific regions of the plaque (the fibrotic cap and the shoulder regions). Granzyme B staining was localized at the internal elastic lamina In order to adhere to the aortic walls, smooth muscle cells require elastin. Aortas of C57 wt, GrB−/−, ApoE−/− and DKO mice were stained with elastic van Gieson (FIGS. 5A to 5D). The aortic wall of the ApoE mouse is very thin and elastin staining is markedly reduced compared to the C57 wt. In the DKO mouse, the aorta wall is significantly thicker and elastin staining is correspondingly more intense. GrB also colocalizes with the internal elastic lamina of atherosclerotic plaques and an influx of macrophages in the ApoE−/−. Surprisingly, this colocalization is not observed in the DKO mice, as demonstrated by confocal microscopy staining.

The increased localization of granzyme B with the internal elastic lamina indicates that it may accumulate on elastin fibres and over time, contribute to degradation of elastin. This in turn would lead to reduced elasticity, production of fragments that enhance inflammation, increased calcification and overall stiffness (hardening) of blood vessels. Reduced elastin in the internal elastic lamina also promotes migration of smooth muscle cells in to the intima (intimal hyperplasia) and the formation of atherosclerotic plaques. The fragmented and degraded elastin (by granzyme B) may lead to recruitment of immune cells of the lesion.

Example 3

Granzyme B Binds to the Extracellular Matrix Protein Elastin

An in vitro granzyme B elastin binding assay was conducted in the following manner. Granzyme B at 50, 100 and 300 ng was incubated with 15 µg of human insoluble skin (Sk) and aortic (Ao) elastin (Elastin Products Company™, Owensville, Mo.) in PBS for three hours at room temperature. The samples were centrifuged at 1000×g at room temperature for three minutes and the insoluble elastin collected in the pellet. The supernatants, which contained unbound granzyme B, were denatured with SDS loading buffer and run on a 10% SDS-PAGE gel. Granzyme B was detected by Western blot. Each gel contained three lanes: a first lane related to a sample containing granzyme B in the absence of elastin; a second lane related to the samples containing granzyme B and human insoluble skin elastin; and a third lane related to the sample containing granzyme B and aortic elastin. The lane relating to the sample containing granzyme B in the absence of elastin showed a heavy band in the supernatant and a faint band in the pellet. The lanes relating to the samples containing granzyme B and skin elastin, and granzyme B and aortic elastin both showed heavy bands in the pellet, which bands were much heavier than the faint band seen in the pellet relating to the sample containing granzyme B in the absence of elastin. Furthermore, the band in the supernatant for the sample containing granzyme B and skin elastin was dramatically less pronounced than the supernatant band shown in the sample relating to granzyme B in the absence of elastin. No band appeared in the supernatant sample containing granzyme B and aortic elastin. Hence, there is less granzyme B present in the supernatant, thus indicating that granzyme B was associating with the elastin in the pellet. This phenomenon was dose-dependent and not restricted to the type of elastin used (i.e. skin elastin or aortic elastin).

Example 4

Granzyme B Cleaves Extracellular Matrix Proteins

Treatment of human coronary artery smooth muscle cells (SMC) matrix with granzyme B induced a cleavage of a number of extracellular proteins. Extracellular proteins from SMC cultures were biotinylated and incubated with granzyme B. The supernatant was collected at 2, 4 and 24 hours after treatment, and the entire insoluble extracellular protein preparation collected at 24 hours. Extracellular proteins were visualized by Western blot for biotin. Western blot for beta-actin confirmed that the extracellular protein preparation was devoid of intercellular proteins. Western blots for fibronectin, phosphorylated FAK (p-FAK), and FAK were also performed on lysates of SMC treated with granzyme B. In the collected insoluble proteins, four protein bands between approximately 50-70 kDa and approximately 236 kDa disappeared 24 hours after treatment with granzyme B and cleavage of fragments approximately 25-39 kDa were evident in the matrix at this same time point. Further, the six proteins and/or cleavage fragments ranging in molecular weight from approximately 29-148 kDa were eluted into the supernatant as early as two hours after granzyme B treatment. To ensure that the SMC extracellular protein preparations used were devoid of intracellular proteins, Western blotting for beta-actin was performed on the collected supernatant and extracellular proteins. Beta-actin was apparent in SMC lysates (positive control) but was absent from matrix and supernatant preparations.

To identify extracellular proteins that are cleaved by granzyme B, western blots for fibronectin, collagen, and vitronectin on lysates from untreated and granzyme B-treated SMCs were performed. In all SMCs treated with granzyme B for 24 hours, there was a reduction in the total amount of fibronectin in lysates collected from SMCs. In the supernatants of granzyme B-treated SMCs at 24 hours, a fibronectin cleavage product was detected. There was no cleavage of collagen IV or vitronectin observed. Therefore, granzyme B induces a cleavage of fibronectin in SMC extracellular matrixes but does not affect collagen IV or vitronectin.

Example 5

Granzyme B Binds and Degrades Elastin in Vitro

Figure 6:
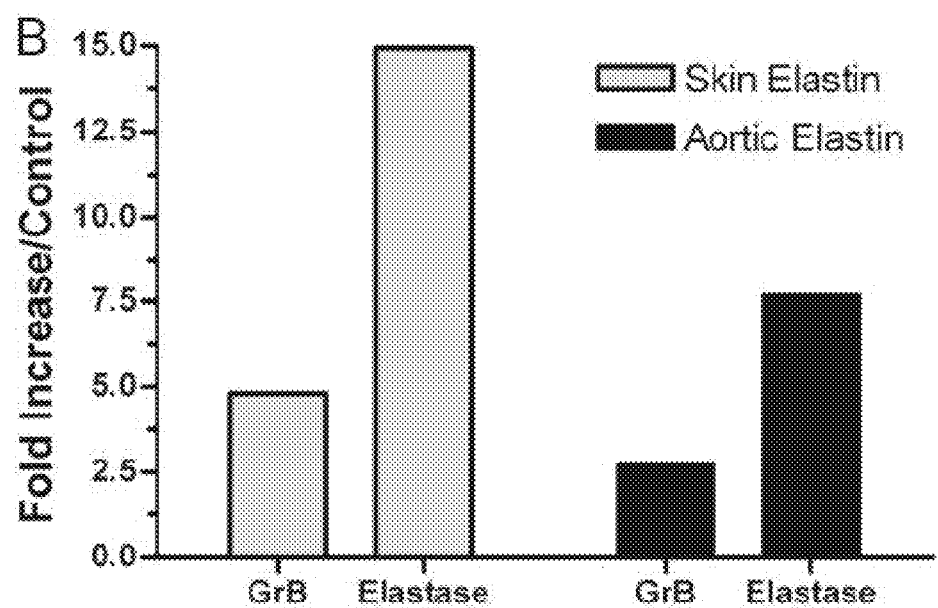
FIG. 6 Granzyme B degrades elastin in vitro. Granzyme B was incubated with $^3$H-elastin for 7 days at room temperature. Elastase was incubated with $^3$H-elastin for 2 hours. Supernatants containing the soluble elastin cleavage fragments were collected and counted. Data is represented as fold increase in radioactivity over the control (elastin only). (n=2).

Tritiated elastin was prepared with the modifications as described in Banda, M. J. and Werb, Z. (1981) *Biochem, J.* 193: 589-605 and Gordon, S., Werb, Z. and Cohn, Z. A. (1976) in *In Vitro Methods in Cell Mediated and Tumor Immunity*, eds. Bloom, B. R. and David, J. R. (Academic Press, New York), pages 349-350. 1 mg of skin or aortic elastin was diluted in 1 ml $dH_2O$ and pHed to 9.2. 1 mCi $NaB_3H_4$ (PerkinElmer™, Waltham Mass.) and 2 mg of non-radioactive $NaB_3H_4$ (Sigma™, St. Louis, Mo.) was added. After 2 hours of incubation, the pH was adjusted to 3.0 and the elastin was incubated for an additional 30 minutes. The elastin was centrifuged for 3 minutes at 5000×g and the pellet was repeatedly washed to remove excess $NaB_3H_4$. For the cleavage assays, 0.15 mg $^3$H-elastin was incubated with granzyme B (0.75 µg was added a total of 5 times) at room temperature for 7 days. At day 7 of incubation, 25 µg of elastase (Elastin Products Company™, Owensville, Mo.) was incubated with elastin for 2 hours, as a positive control. After incubations, reactions were centrifuged at 5000×g for 3 minutes. The radioactivity of the soluble, cleaved elastin fragments in the supernatant was counted in Ready Safe Scintillation Fluid (Beckman-Coulter™, Fullerton, Calif.). The radioactivity of the cleaved, soluble elastin fragments was 4.8 times and 2.7 times higher than background for skin and aortic elastin, respectively (FIG. 6). Proteolysis of elastin by elastase yielded a radioactivity increase over background of 14.9 fold for skin elastin and 7.7 fold for aortic elastin. These data show that granzyme B has affinity to elastin and has elastolytic activity.

Example 6

Figure 7:
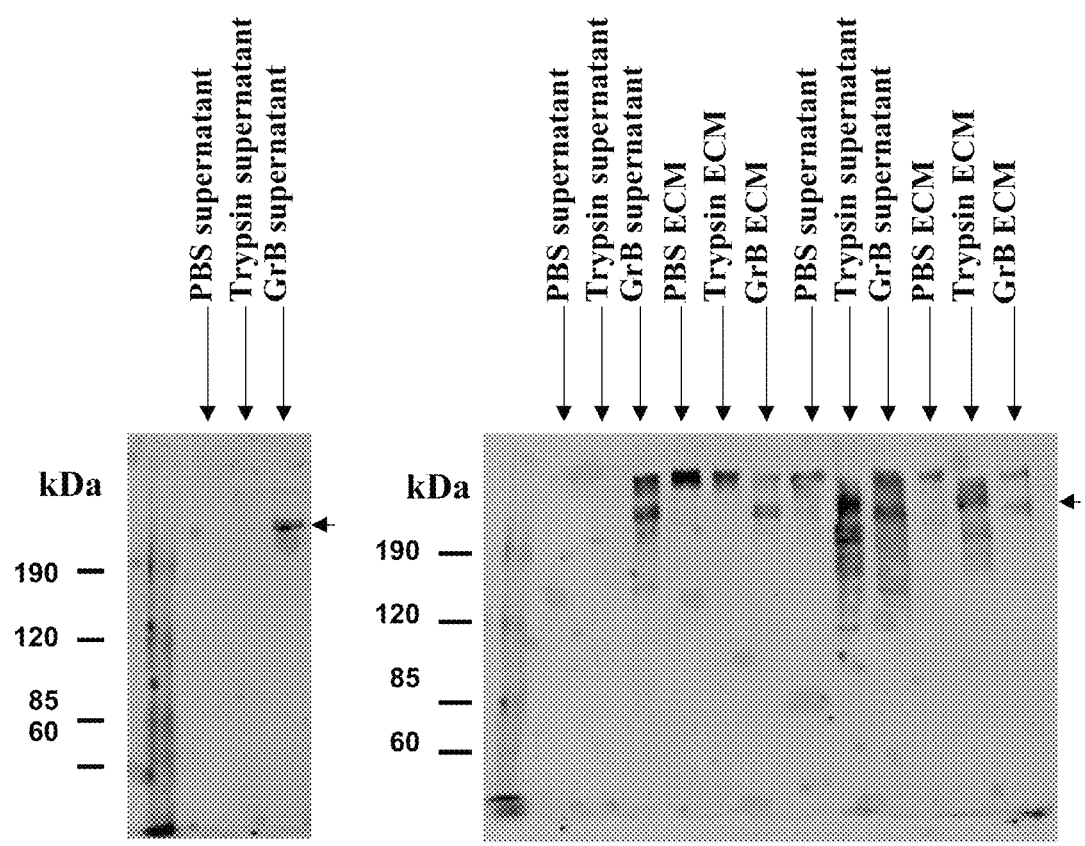
FIG. 7 Illustrates three representative groups of Western blots showing that granzyme B cleaves fibrillin-1.
Figure 8:
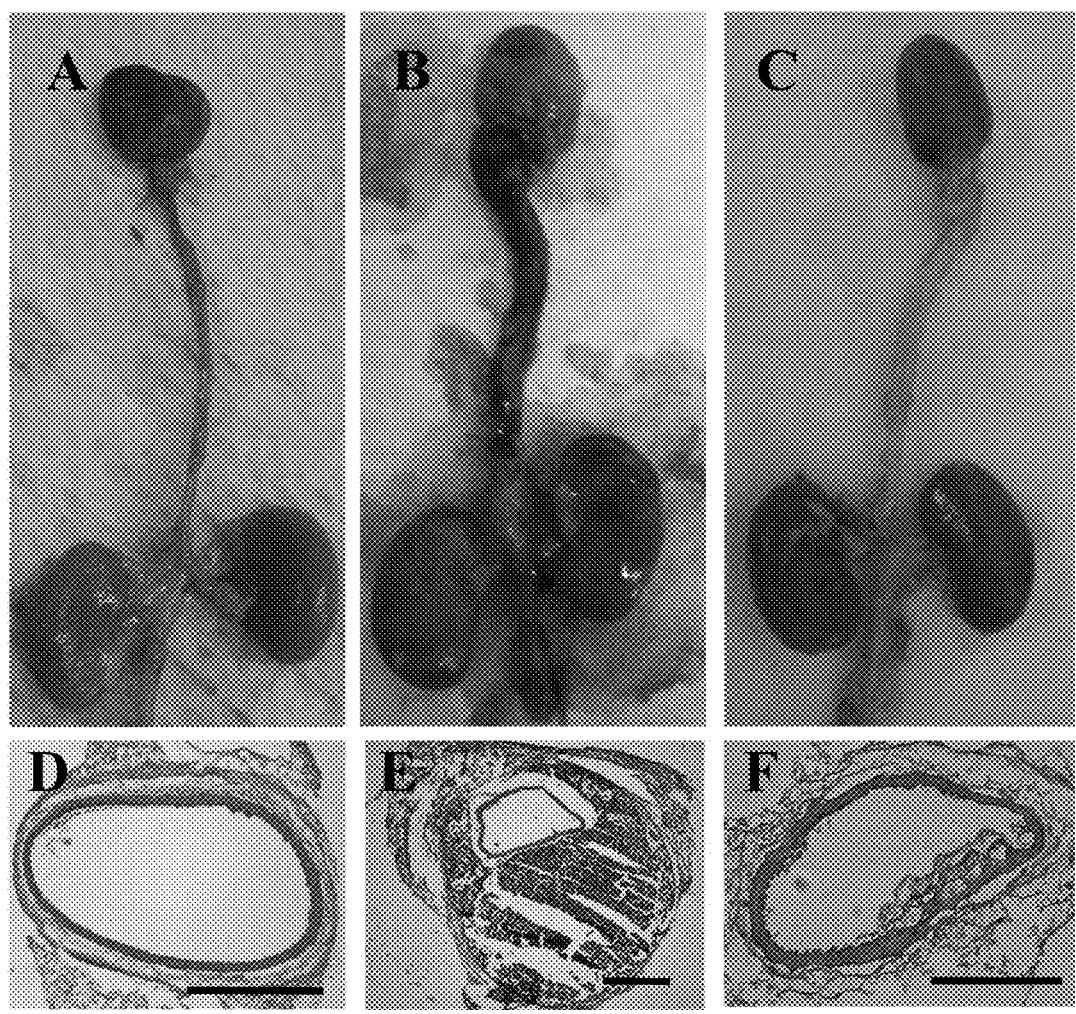
FIG. 8A Illustrates an aorta from C57 mouse infused with angiotensin II (AngII).
FIG. 8B Illustrates an aorta from an apoE-KO mouse infused with AngII.
FIG. 8C Illustrates an aorta from a GrB/apoE-DKO mouse infused with AngII.
FIG. 8D Illustrates H&E staining of an aorta cross-section from a C57 mouse infused with AngII (10× magnification). Scale bar=500 µm.
FIG. 8E Illustrates H&E staining of an aorta cross-section from an apoE-KO mouse infused with AngII (4× magnification). Scale bar=500 µm.
FIG. 8F Illustrates H&E staining of an aorta cross-section from a GrB/apoE-DKO mouse infused with AngII (10× magnification). Scale bar=500 µm.
Figure 9:
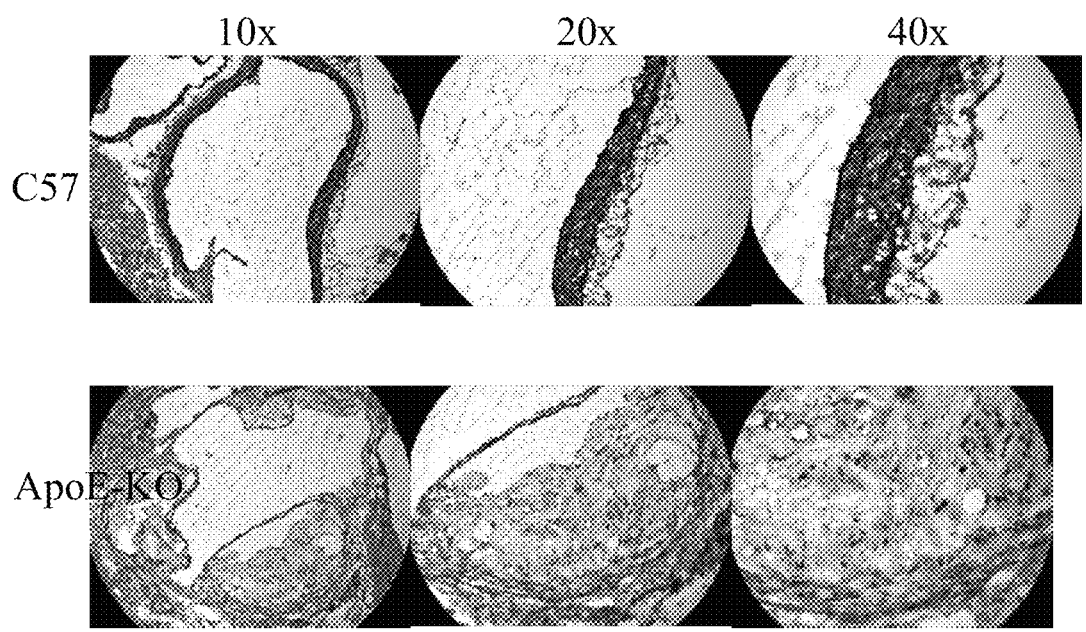
FIG. 9 Illustrates reduced fibrillin-1 staining as observed in ApoE-KO mice compared to C57 mice.

Human coronary artery smooth muscle cells were cultured to confluency and serum starved for 48 hours at which time cells were lysed with $NH_4OH$ so that the intact extracellular matrix (ECM) remained on the plate. Granzyme B (80 nm) was incubated on the ECM for 24 hours at room temperature. Supernatants (containing cleaved ECM) and ECM still attached to the plate were collected and assessed for fibrillin cleavage by Western blot. The results are shown in FIG. 7. The arrows in FIG. 7 indicate fibrillin-1 cleavage fragments. 6 independent experiments were carried out and 3 representative groups are shown in FIG. 7.

Example 7

Aortic dissections were induced with 28 day infusion of 2000 ng/kg/min angiotensin-II dissolved in saline, or placebo, through an ALZET™ osmotic pump (model 1004). The pumps were implanted into the subcutaneous space in the upper dorsal regions through a small incision site at the back of the neck of the anesthetized mouse, and the incision was closed with dissolving sutures. The mice were euthanized by carbon dioxide inhalation followed by cardiac puncture 28-days post implantation. The thoracic cavity and abdominal cavity were then opened, and the circulation perfused with PBS via a cannula placed in the left ventricle, with fluid drained from a severed right atria. Following PBS perfusion, fresh 10% formalin was perfused in the same manner. The heart, kidneys and entire aorta to the iliac bifurcation was then carefully dissected from the animal, and photographed en masse. Sections from the abdominal aorta were then mounted in OCT, frozen to −80, sectioned, and stained with standard H&E. The results are illustrated in FIGS. 8A to 8F and 9.

Figure 10:
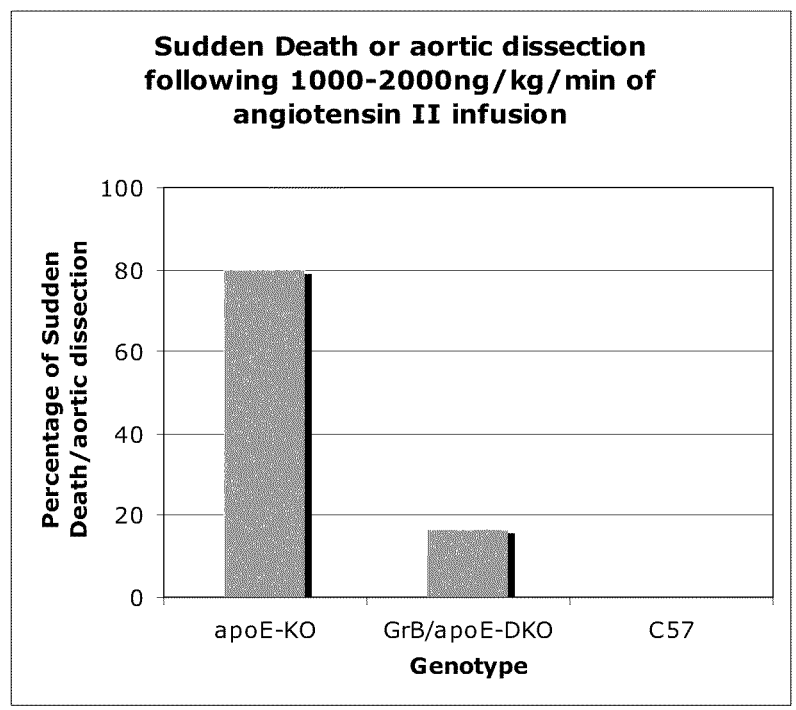
FIG. 10 Shows a chart illustrating and comparing the percentage of sudden deaths/aortic dissections in a three different genotypes of mouse following AngII infusion.

ApoE/GrD-DKO mice are protected from aortic dissections and sudden death. Angiotensin-II (angII) infusion induces aortic dissections in apoE-KO mice. Aortic dissections were defined by blood accumulation between the media and outer aortic wall. Mice that were found dead without any preceding signs of suffering were defined as sudden death. After chronic infusion of angII, seven of eight (87.5%) of apoE-KO mice developed aortic dissections or succumbed to sudden death. Four of eight (50%) underwent sudden death before the 28-day time point due to rupturing of the thoracic aorta, one was euthanized due to lower limb paralysis, two survived to 28-day time point but developed aortic dissections, one showed no visible signs of aortic dissections. In contrast, zero of six wildtype, and one of seven (14%) GrB/apoE-DKO succumbed to sudden death, and none developed aortic dissections. No sudden death or aortic dissections were observed in any mice in the saline control groups (n=6 for all groups). These results are shown graphically in the chart in FIG. 10.

Example 8

Implantation of Osmotic Mini Pump and Survival Following Angiotensin II Infusion We successfully optimized the implantation of ALZET® 1004 minipumps into our three month old mice. There was a 0% mortality rate from surgical complications. One mouse was euthanized early due to observed weight loss attributed to a mal-occluded tooth, and this animal was discarded from all of our data analysis. Table 1 details the ages of mice at time of implant, start and change in weight, and number surviving to 28 days. Mice were slightly older in the angII infusion GrB/apoE-DKO group, due to availability of litters. The ALZET® 1004 minipumps contained either 100 µL of saline or angiotensin II. The pumps remained in the animal for the remainder of the 28 day experiment.

TABLE 1

Summary of Animals Used in this Study

| Genotype | Treatment | n at 0 days | n at 28 days | Average age (days) | Starting weight (g) | Weight change (g) |
|---|---|---|---|---|---|---|
| apoE-KO | saline | 8 | 8 | 109.8 | 27.7 | 1.3 |
| apoE-KO | angII | 16 | 9 | 104.3 | 28.2 | 1.0 |
| GrB/apoE-DKO | saline | 11 | 11 | 112.7 | 29.8 | 1.2 |
| GrB/apoE-DKO | angII | 15 | 13 | 136.1 | 29.1 | −0.3 |

Table 1. A total of 50 male mice were used in this study. 24 apoE-KO mice received either saline or angII, and 26 GrB/apoE-DKO mice received either saline or angII. The starting ages and weights are listed for all mice.
The weight change value is calculated from only the mice that survived to the 28-day time point.
Abbreviations:
angII, angiotensin II;
apoE-KO, apolipoprotein E-knockout;
GrB/apoE-DKO, granzyme B/apoE-double knockout mouse.

Figure 11:
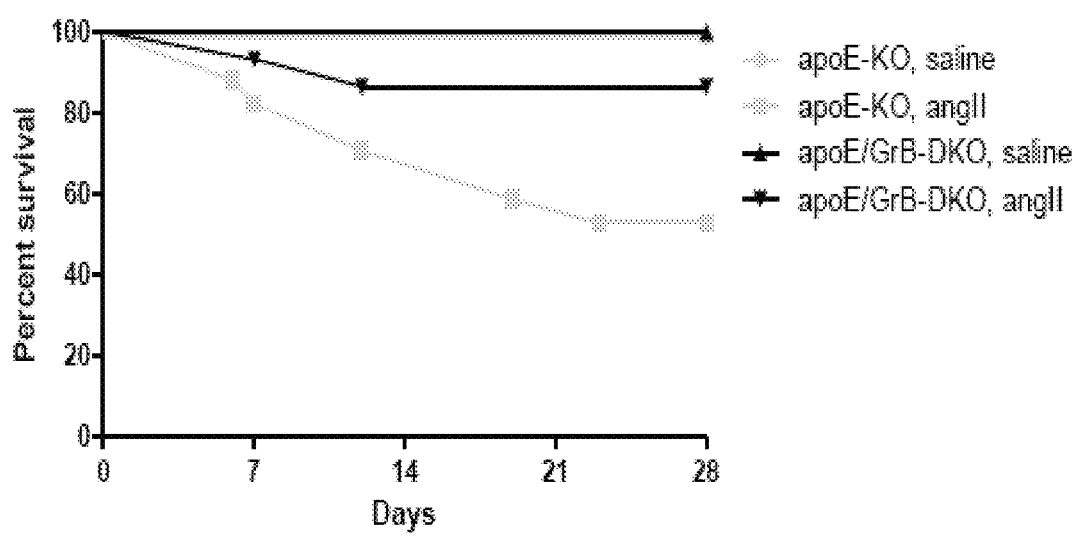
FIG. 11 Shows a Kaplan-Meier Survival Curve for apoE-KO and GrB/apoE-DKO mice given saline or angiotensin II. Abbreviations: angII, angiotensin II; apoE-KO, apolipoprotein E-knockout; GrB/apoE-DKO, granzyme B/apoE-double knockout mouse.

FIG. 11 shows a Kaplan-Meier curve detailing the survival over the 28 day experiment. No mortality was observed in either group infused with saline, and GrB/apoE-DKO mice had a significant increase in survival (83%) versus apoE-KO mice (56%) to 28-days with chronic angII infusion. Lines represent percentage of mice alive on each day. No death was observed in either control group (n=8 for apoE-KO, n=11 for GrB/apoE-DKO. In contrast, 86.67% of GrB/apoE-DKO (n=15) and 56.25% of apoE-KO mice (n=16) infused with angII survived to 28 days. Curves were significantly different, as measured by the Log-rank (Mantel-Cox) Test (p=0.0037).

Example 9

Angiotensin II Associated Pathology is Decreased in GrB/apoE-DKO Mice

Figure 12:
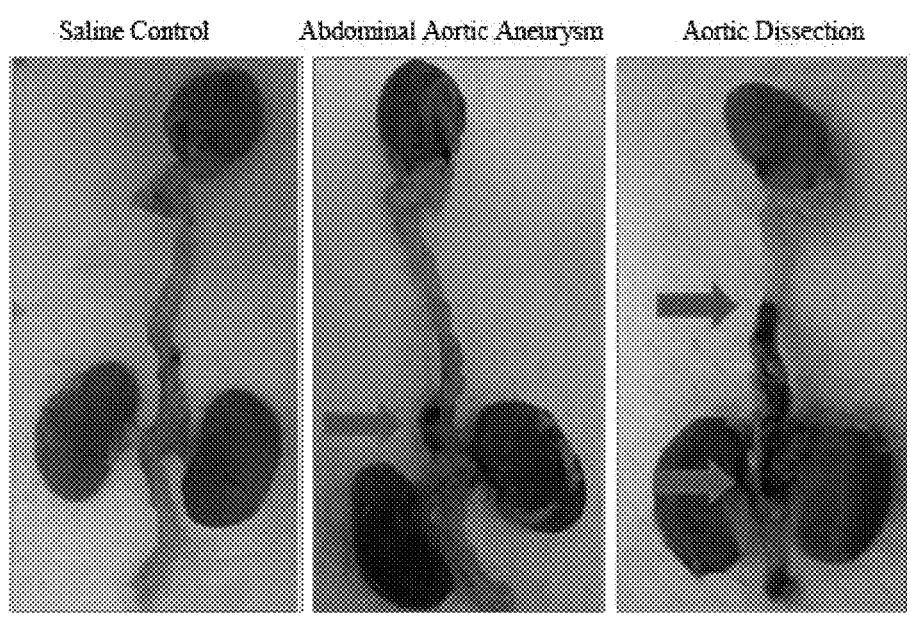
FIG. 12 Shows gross pathology of aortas in tissues at day 28 in surviving mice for a saline control, abdominal aortic aneurysm and aortic dissection. Blood was collected by cardiac puncture following $CO_2$ euthanization. The single arrow shows an aortic aneurysm the dissection length is indicated by 2 arrows. Abbreviations: apoE-KO, apolipoprotein E-knockout; GrB/apoE-DKO, granzyme B/apoE-double knockout mouse.
Figure 13:
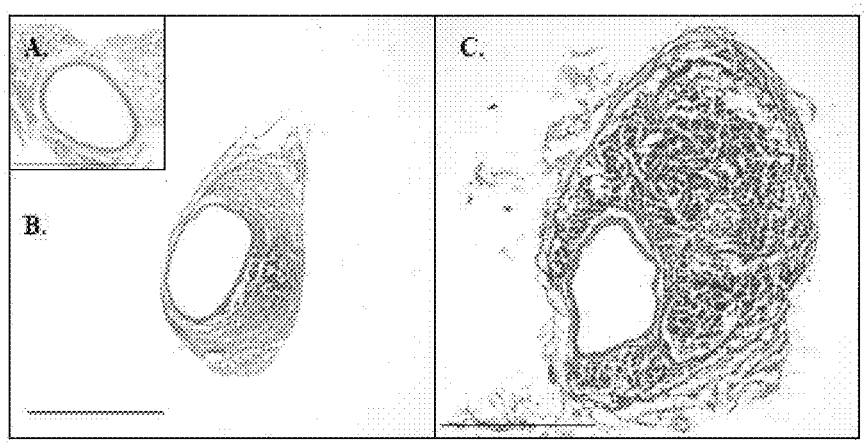
FIG. 13 Shows H&E staining of representative abdominal aortas for A. normal, a healthy blood vessel, B. a vessel with a small medial thrombus, indicative of a small aneurysm, and C. a vessel with a large amount of blood in the media, indicative of a large dissecting aneurysm. Scale bar=1000 mm.

FIG. 12 shows characteristic gross pathology assessed at 28 days. Aortic dissections were defined by blood accumulation between the media and outer aortic wall, and abdominal aneurysms were defined by the presence of a small, medial thrombus. Mice that were found dead without any preceding signs of suffering were defined as sudden death. Blood was collected by cardiac puncture following CO2 euthanization. The mouse was placed on ice, the chest was opened, the right atrium was cut, and a needle was placed in the left ventricle. Saline, and then 4% para-formaldehyde, were perfused at a constant pressure of 100 mmHg until no blood is observed exiting the incision in the right atria. The heart, aorta to the iliac bifurcation, and kidneys were dissected from the mouse and photographed. A healthy aorta is shown in the left panel, which is representative of what was observed in all saline infused animals. An aorta with an abdominal aortic aneurysm is shown in the middle panel (indicated by arrow), which is representative of 30% of the GrB/apoE-DKO mice. An aorta with an aortic dissection is shown in the far right panel (dissection length indicated by 2 arrows), which is representative of what was observed in the majority of surviving apoE-KO mice. FIG. 13 shows representative H&E images of a healthy aorta, a small AAA, and a large aortic dissection.

Figure 14:
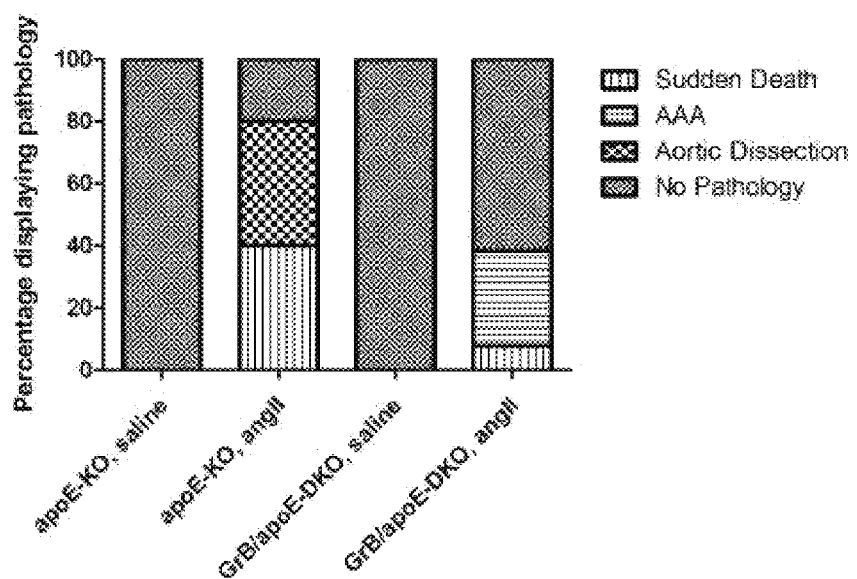
FIG. 14 Shows a bar graph of the gross pathological outcomes for apoE-KO and GrB/apoE-DKO mice given saline or angiotensin II. Abbreviations: AAA, abdominal aortic aneurysm; angII, angiotensin II; apoE-KO, apolipoprotein E-knockout; GrB/apoE-DKO, granzyme B/apoE-double knockout mouse.
Figure 15:
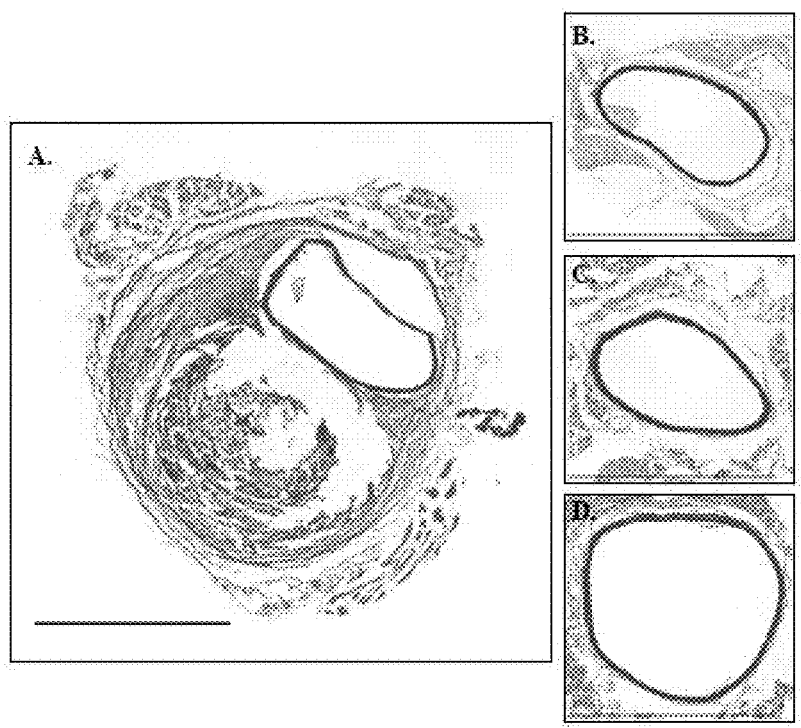
FIG. 15 Shows Movat's pentachrome staining of abdominal aortas for A. apoE-KO, angII; B. apoE-KO, saline; C. GrB/apoE-DKO, saline; D. GrB/apoE-DKO, angII mice. Scale bar=1000 µm. Abbreviations: AAA, abdominal aortic aneurysm; angII, angiotensin II; apoE-KO, apolipoprotein E-knockout; GrB/apoE-DKO, granzyme B/apoE-double knockout mouse.

The differences in pathological outcome are shown graphically in FIG. 14, where no pathology was observed with either saline group. The surviving mice in the apoE-KO angII group developed aortic dissections in contrast to the small AAA observed in 30% of the GrB/apoE-DKO surviving group. FIG. 14, shows the outcome of all mice used in experiment and sudden death was defined as mice that expired without any signs of suffering. On necropsy, it appeared that death was caused by a rupture of the aorta, in all but one of the apoE-KO mice and the single GrB/apoE-DKO mouse that died early. Our pathological assessments were confirmed by H&E and Movat's staining of cross sections from thoracic and abdominal aortas (FIG. 15). FIG. 15 shows no pathology with saline infused mice in either the apoE-KO or the GrB/apoE-DKO groups. Following 28-days of angII infusion, most apoE-KO surviving mice displayed a dissecting aneurysm. However, the GrB/apoE-DKO mice displayed no pathology, or small AAAs.

Over the 28-day experiment, GrB-deficiency caused a significant increase of survival (83%) over apoE-KO mice that still possessed GrB (53%). GrB/apoE-DKO mice that did develop AAA were very small, early stage AAA that did not dissect. This was in contrast to the AAA observed in the apoE-KO mice that were larger and had dissected. When the apoE-KO mice that died early during the experiment were examined, large blood clots were found in the thoracic cavity. Often, the aorta was also dissected up to the level of the heart, suggesting that death was caused by rupturing of the aorta. In turn, suggesting that GrB plays an important, detrimental role in the development of AAA and the progression of dissecting AAA, and that its deficiency is protective. In addition, a lack of fibrillin-1 staining in the aortas of apoE-KO mice compared to GrB/apoE-DKO mice and as taught herein, that GrB can cleave fibrillin-1 in vitro, it appears that GrB contributes to aneurysm and dissection formation and progression by cleaving fibrillin-1.

Example 10

AT1 Receptor in Transgenic Mice

Immunohistochemistry revealed the presence of the AT1 receptor in both the apoE-KO and GrB/apoE-DKO vessels, and also in the wildtype mouse (C57), which was used as a positive control. This result verified that the AT1 receptor was not inadvertently affected during the generation of the transgenic strains.

Example 11

Thoracic and Abdominal Aortic Lumen Area

Figure 16:
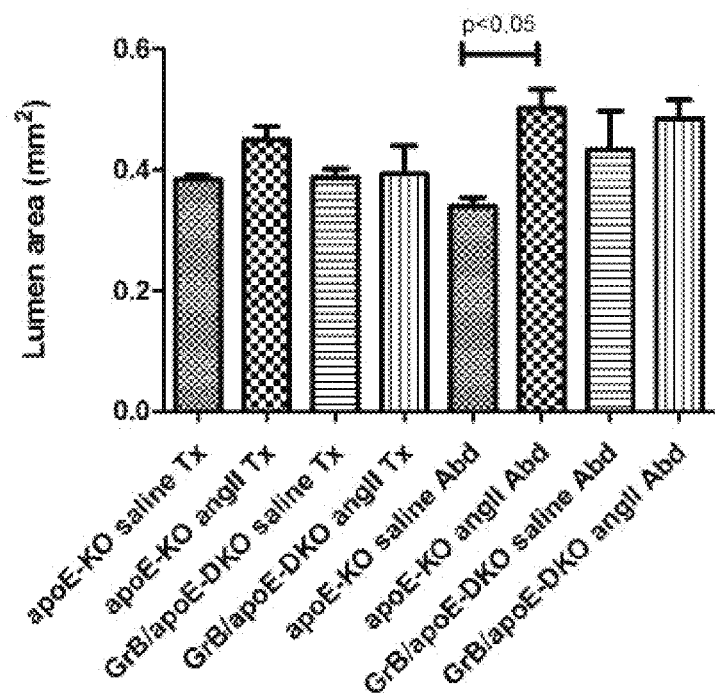
FIG. 16 Shows lumen area of thoracic and abdominal aortas from apoE-KO and GrB/apoE-DKO mice given saline or angiotensin II. Bars represent mean value, error bars represent standard error of the mean (SEM). Abbreviations: Abd, abdominal aorta; angII, angiotensin II; apoE-KO, apolipoprotein E-knockout; GrB/apoE-DKO, granzyme B/apoE-double knockout mouse; Tx, thoracic aorta.

FIG. 16 shows the dimensions of the thoracic and abdominal aortas, expressed in area. A one-way ANOVA/Dunn's Multiple Comparison Test was performed to compare all values. The only statistically significant difference (p<0.05) was between the abdominal lumen area of apoE-KO mice that received saline or angII for 28 days. Samples were collected following 28 days of angII or saline infusion. Formalin fixed tissue was embedded in OCT, sectioned on a cryostat, and stained with Movat's pentachrome. The internal elastic lamina was traced using ImageProPlus™, and the maximum diameter was calculated. AngII caused a statistically significant increase between apoE-KO abdominal samples (one-way ANOVA/Dunn's Multiple Comparison Test, p<0.05). Bars represent mean value, error bars represent standard error of the mean (SEM).

Example 12

Angiotensin II Causes Medial Thickening

Figure 17:
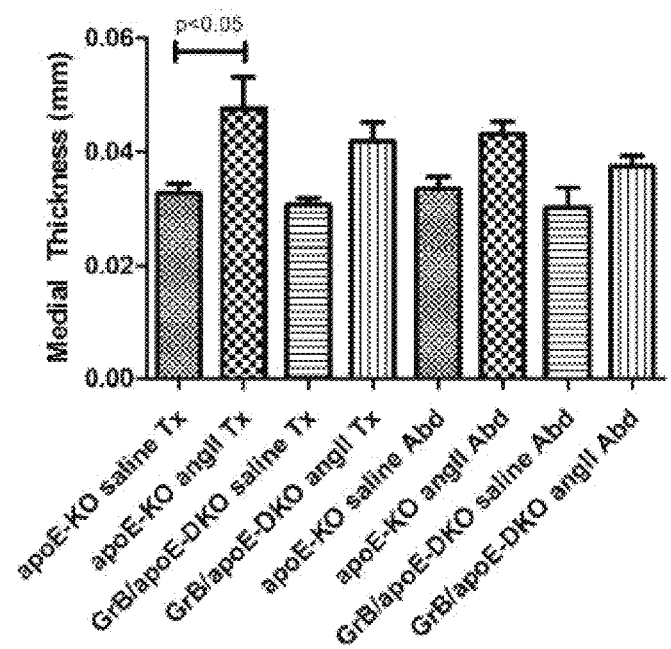
FIG. 17 Shows medial thickness of thoracic and abdominal aortas in apoE-KO and GrB/apoE-DKO mice given saline or angiotensin II. Abbreviations: Abd, abdominal aorta; angII, angiotensin II; apoE-KO, apolipoprotein E-knockout; GrB/apoE-DKO, granzyme B/apoE-double knockout mouse; Tx, thoracic aorta.

The medial thickness of both the thoracic and abdominal samples was measured. Although not significant, except for the apoE-KO saline versus angII thoracic samples (p<0.05), there is a trend for medial thickness to increase following angII infusion, as was expected in the literature (FIG. 17). Samples were collected following 28 days of angII or saline infusion. Formalin fixed tissue was embedded in OCT, sectioned on a cryostat, and stained with Movat's pentachrome. The internal and external elastic lamina were traced with ImageProPlus™. The medial thickness was calculated by subtracting the maximum area calculated from the external elastic lamina from the maximum area calculated from the internal elastic area, and then dividing by internal elastic lamina perimeter value. Bars represent mean values, error bars represent standard error of the mean (SEM). Statistically significant differences were only achieved between the thoracic values for apoE-KO mice (one-way ANOVA/Dunn's Multiple Comparison Test, p<0.05). Although not statistically significant, there is a trend for angII infusion to increase medial thickness.

Example 13

Aortic Root Atherosclerosis

Figure 18:
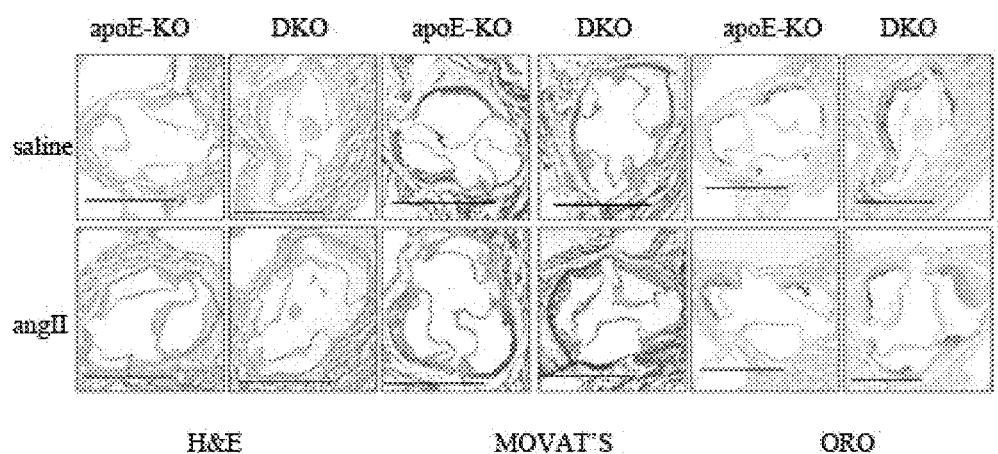
FIG. 18 Shows aortic roots in apoE-KO and GrB/apoE-DKO mice stained by H&E, Movat's and ORO. Scale bar=1 mm. Abbreviations: angII, angiotensin II; apoE-KO, apolipoprotein E-knockout; DKO, granzyme B/apoE-double knockout mouse; H&E, Hematoxylin and eosin; ORO, Oil red O.
Figure 19:
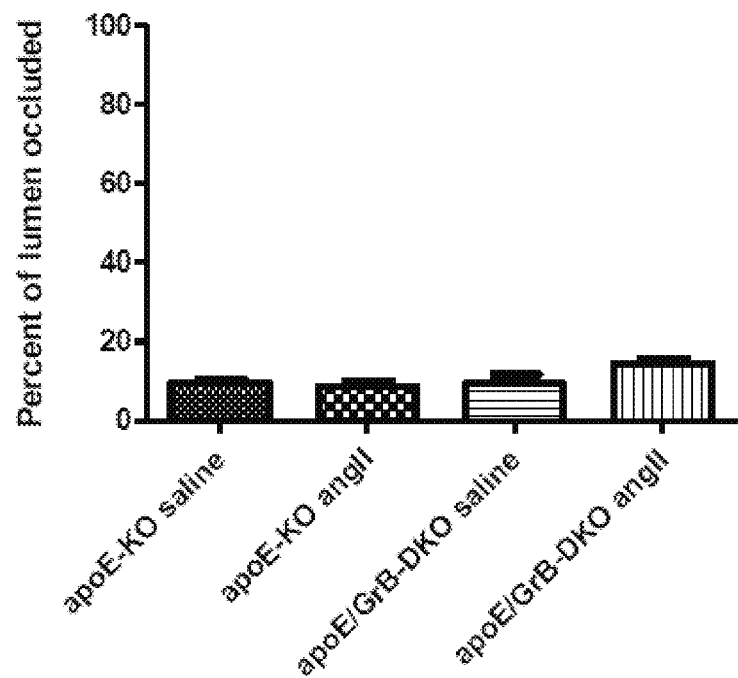
FIG. 19 Shows measurements of aortic root lumen and plaques for apoE-KO and GrB/apoE-DKO mice surviving to 28 days given saline or angiotensin II (apoE-KO saline, n=7; GrB/apoE-DKO saline, n=7; apoE-KO angII, n=9; GrB/apoE-DKO, n=11). Bars represent percentage of aortic root lumen covered by plaque, error bars represent standard error of mean (SEM). Abbreviations: angII, angiotensin II; apoE-KO, apolipoprotein E-knockout; GrB/apoE-DKO, granzyme B/apoE-double knockout mouse.

No significant differences were observed between the amount of atherosclerosis present in the aortic root between the 4 groups (p>0.05) (FIG. 18). In FIG. 18, formalin fixed hearts collected from mice that survived to 28 days were embedded in OCT, and sectioned on the cryostat. Slides were stained with H&E, Movat's, and ORO. When the aortic root lumen area and plaque area were obtained, no significant difference was observed in calculated percent lumen covered by plaque between either genotype on either treatment. FIG. 19 represents the percentage of plaque in the lumen. No significant difference was observed with lumen or plaque measurements (p>0.05). In FIG. 19, aortic roots were collected from animals surviving to 28 days. No significant difference was observed between either genotype on either treatment (one-way ANOVA/Dunn's Multiple Comparison Test, p>0.05). Each experimental group is made from 10-20 sections per mouse, and each group had 7-11 mice per group (apoE-KO saline, n=7; GrB/apoE-DKO saline, n=7; apoE-KO angII, n=9; GrB/apoE-DKO, n=11).

Example 14

GrB/apoE-DKO Mice and Fibrillin-1 Expression

Figure 20:
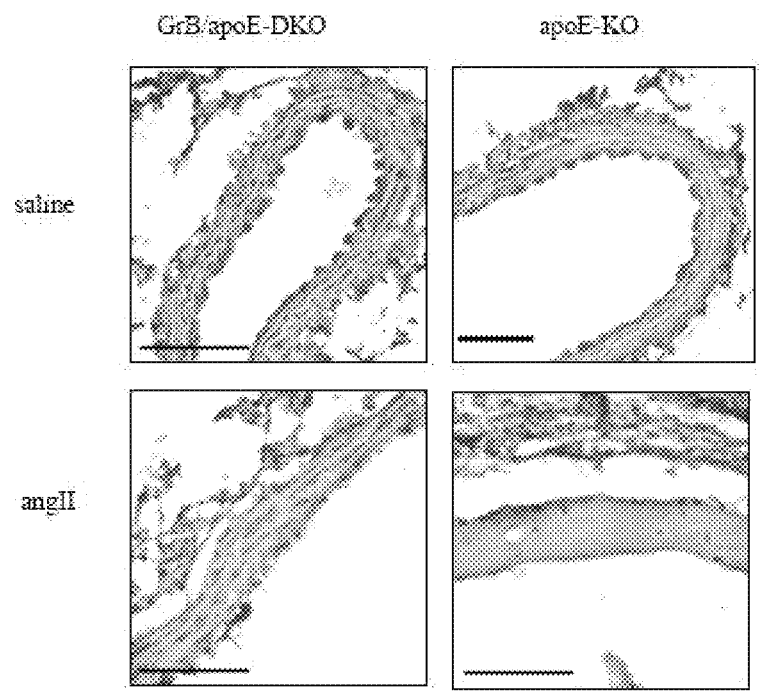
FIG. 20 Shows fibrillin-1 staining in abdominal aorta from apoE-KO and GrB/apoE-DKO mice. Scale bar=100 µm. Abbreviations: angII, angiotensin II; apoE-KO, apolipoprotein E-knockout; GrB/apoE-DKO, granzyme B/apoE-double knockout mouse.

Staining with antifibrillin-1 revealed a greater amount of fibrillin-1 in GrB/apoE-DKO mice versus apoE-KO in both saline and angII treatment groups (FIG. 20). Interestingly, in areas around the thrombus of an AAA or dissection, very minimal fibrillin-1 staining was observed (FIG. 20, bottom right panel). Samples were collected following 28 days of angII or saline infusion. Formalin fixed tissue was embedded in optimal cutting temperature (OCT), sectioned on a cryostat, and stained with anti-fibrillin-1. Decreased fibrillin-1 staining, as indicated by red colour, was observed in apoE-KO mice from saline and angII-infusion, versus GrB/apoE-DKO mice.

Example 15

GrB Staining in Human Aneurysm

Figure 21:
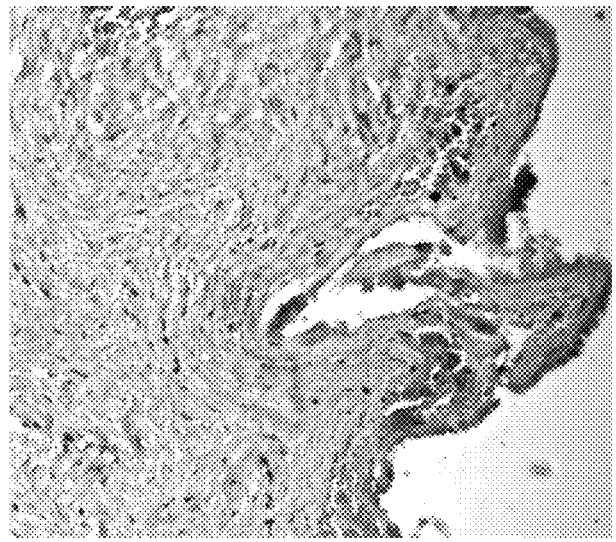
FIG. 21 Shows A. human abdominal aortic aneurysm tissue stained with secondary antibody only and B. human abdominal aortic aneurysm tissue stained for GrB, with arrows indicating areas of intense GrB staining in the aneurysm tissue.
Figure 21:
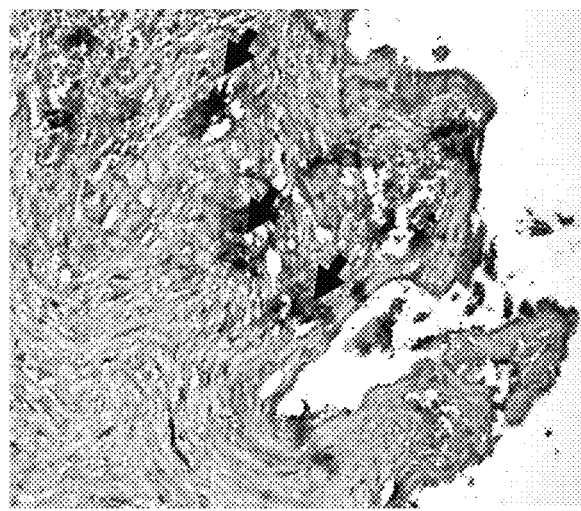

FIG. 21 shows human abdominal aortic aneurysm tissue stained with secondary antibody only A. and human abdominal aortic aneurysm tissue B. stained for GrB. Arrows indicate areas of intense GrB staining in the aneurysm tissue that is not observed in healthy arteries (data not shown). Furthermore, staining of GrB has also been shown to have extracellular localization (data not shown).

What is claimed is:

1. A method of preventing progression of a vasculopathy or treating a vasculopathy in a subject in need thereof, the method comprising:

selecting a subject having a Granzyme B plasma concentration of greater than 40 pg/ml and a fibronectin plasma concentration of >400 μg/ml; and administering to the selected subject a therapeutically effective amount of a Granzyme B inhibitor, thereby treating a vasculopathy or preventing progression of a vasculopathy in the subject.

2. The method of claim 1, wherein the vasculopathy is selected from one or more of the group consisting of atherosclerosis, aneurysm, and dissection.

3. The method of claim 1, wherein the vasculopathy is an aortic aneurysm.

4. The method of claim 1, wherein the vasculopathy is a cerebral aneurysm.

5. The method of claim 1, wherein the vasculopathy is an aortic dissection.

6. The method of claim 1, wherein the vasculopathy is a cerebral dissection.

7. The method of claim 1, wherein the vasculopathy is atherosclerosis.

8. The method of claim 3, wherein the aortic aneurysm has a diameter of at least 3 cm.

9. The method of claim 1, wherein the Granzyme B inhibitor is formulated for oral administration.

10. The method of claim 1, wherein the Granzyme B inhibitor is formulated for administration by injection.

11. The method of claim 1, wherein the Granzyme B inhibitor is formulated for topical administration.

12. The method of claim 1, wherein the Granzyme B inhibitor is formulated for topical application to a device.

13. The method of claim 12, wherein the device is selected from the group consisting of a stent, a clip, a catheter, and a coil.

14. The method of claim 1, wherein the subject is a human.

15. The method of claim 1, wherein administering is to the tissue of the blood vessel or intima of the subject.

16. The method of claim 1, wherein the plasma concentration of Granzyme B is determined by immunodiagnostic assay.

17. The method of claim 1, wherein the plasma concentration of fibronectin is measured by immunodiagnostic assay.

18. The method of claim 16 or 17, wherein the immunodiagnostic assay is an enzyme-linked immunosorbent assay.

19. The method of claim 1, further comprising one or more diagnostic assessment selected from the group consisting of a diagnostic imaging assessment, a clinical diagnostic assessment, and an alternative laboratory diagnostic assessment.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Mus musculus

<400> SEQUENCE: 1
tgaagatcct cctgctactg c                                            21

<210> SEQ ID NO 2
<211> LENGTH: 20
<212> TYPE: DNA
<213> ORGANISM: Mus musculus

<400> SEQUENCE: 2
tcctgagaaa gacctctgcc                                              20

<210> SEQ ID NO 3
<211> LENGTH: 20
<212> TYPE: DNA
<213> ORGANISM: Mus musculus

<400> SEQUENCE: 3
gcctagccga gggagagccg                                              20

<210> SEQ ID NO 4
<211> LENGTH: 22
<212> TYPE: DNA
<213> ORGANISM: Mus musculus

<400> SEQUENCE: 4
tgtgacttgg gagctctgca gc                                           22